US008562949B2

(12) United States Patent
Kung et al.

(10) Patent No.: US 8,562,949 B2
(45) Date of Patent: Oct. 22, 2013

(54) RADIOLABELED DIHYDROTETRABENAZINE DERIVATIVES AND THEIR USE AS IMAGING AGENTS

(75) Inventors: Hank F. Kung, Wynnewood, PA (US); Mei-Ping Kung, Wynnewood, PA (US); Michael Kilbourn, Ann Arbor, MI (US); Daniel M. Skovronsky, Glen Mills, PA (US)

(73) Assignees: The Trustees of the University of Pennsylvania, Philadelphia, PA (US); The Regents of the University of Michigan, Ann Arbor, MI (US); Avid Radiopharmaceuticals, Inc., Philadelphia, PA (US)

( * ) Notice: Subject to any disclaimer, the term of this patent is extended or adjusted under 35 U.S.C. 154(b) by 1627 days.

(21) Appl. No.: 11/797,341

(22) Filed: May 2, 2007

(65) Prior Publication Data
US 2008/0050312 A1 Feb. 28, 2008

Related U.S. Application Data

(60) Provisional application No. 60/908,116, filed on Mar. 26, 2007, provisional application No. 60/796,518, filed on May 2, 2006.

(51) Int. Cl.
A61K 51/00 (2006.01)
A61K 49/04 (2006.01)
C07D 455/06 (2006.01)

(52) U.S. Cl.
USPC .............................. 424/1.89; 424/9.44; 546/95

(58) Field of Classification Search
None
See application file for complete search history.

(56) References Cited

U.S. PATENT DOCUMENTS

| 3,053,845 | A | | 9/1962 | Tretter |
| 4,076,820 | A | | 2/1978 | Archibald et al. |
| 5,278,308 | A | * | 1/1994 | Kung .............................. 546/95 |

FOREIGN PATENT DOCUMENTS

| FR | 2770215 A1 | 4/1999 |
| GB | 1038919 | 8/1966 |
| JP | 2001-521034 | 11/2001 |
| WO | WO 93/16730 | 9/1993 |
| WO | WO 99/21856 | 5/1999 |

OTHER PUBLICATIONS

Tang G, Wang M, Tang X, Luo L, Gan M. Synthesis and evaluation of O-(3-[18F]fluoropropyl)-L-tyrosine as an oncologic PET tracer. 2003 Nucl. Med. Biol. 30: 733-739.*
Kilbourn MR, Lee LC, Heeg MJ, Jewett DM. Absolute configuration of (+)-alpha-dihydrotetrabenazine, an active metabolite of tetrabenazine. 1997 Chirality 9: 59-62.*
Jewett DM, Kilbourn MR, Lee LC. A simple synthesis of [11C]dihydrotetrabenazine (DTBZ). 1997 Nucl. Med. Biol. 24: 197-199.*
Okarvi SM. Recent progress in fluorine-18 labelled peptide radiopharmaceuticals. 2001 Eur. J. Nucl. Med. 28: 929-938.*
Zheng, G. et al. Vesicular Monoamine Transporter 2: Role as a Novel Target for Drug Development, The AAPS Journal 2006; 8(4) Article 78, E682-E692.
Saner, A. et al. A Benzo[a]quinolizine Derivative with a Neuroleptic-Like Action on Cerebral Monoamine Turnover, The Journal of Pharmacology and Experimental Therapeutics 1977; 203(3), 556-563.
Cooper J.R. et al., *Biochemical Basis of Neurochemistry*, 5[th] ed., Oxford University Press, New York, 1986, p. 290.
Darchen F. et al., Quantitative autoradiography of the rat brain vesicular monoamine transporter using the binding of [$^3$H]dihydrotetrabenazine and 7-amino-8-[$^{125}$I]iodoketanserin, *Neurosci.*, 33:341-349, 1989.
Clarke F. H. et al., A series of hexahydro[1,4]oxazino[3,4-a]isoquinolines as potential neuroleptics, *J. Med. Chem.* 21:785-791, 1978.
Henry, J. P., Scherman D., Radioligands of the vesicular monoamine transporter and their use as markers of monoamine storage vesicles, (Commentary) *Biochem. Pharmacol.*, 38:2395-2404, 1989.
Kaiser, C. et al., Antipsychotic Agents, *Burger's Medicinal Chemistry*, 4th Ed., Wolf, M.E., ed., Wiley-Interscience, New York, 1981, pp. 860-980.
Masuo Y. et al., [$^3$H]Dihydro-tetrabenazine, a new marker for the visualization of dopaminergic denervation in the rat stratum. *Neurosci. Lett.*, 114:45-50, 1990.
Meshgin-Azarian S., et al., Distribution of [$^3$H]dihydrotetrabenazine binding in bovine striatal subsynaptic fractions: Enrichment of higher affinity binding in a synaptic vesicle fraction. *J. Neurochem.* 50:824-830, 1988.
Neumeyer, J.L., Neuroleptics and Axiolytic Agents, In *Priniciples of Medicinal Chemistry*, Foye, W. O., ed., Lea and Febiger, Philadelphia, PA, 1981, 199-240.
Near J. A., [$^3$H]Dihydrotetrabenazine binding to bovine striatal subsynaptic vesicles, *Mol. Pharmacol.*, 30:252-257, 1986.
Saner A., Pletscher A., A benzo[a]quinoline derivative with a neuroleptic-like action on cerebral monoamine turnover. *J. Pharmacol. Exp. Ther.* 203:556-563, 1977.
Scherman D. et al., [$^3$H]Dihydrotetrabenazine, a new in vitro monoaminergic probe for human brain, *J. Neurochem.*, 50:1131-1136, 1988.
Suchi R. et al., Covalent modification of the amine transporter with N,N'-dicyclohexylcarbodiimide, *Biochem.*, 30:6490-6494, 1991.
Lednicer D., Mitscher L. A. *The Organic Chemistry of Drug Synthesis*, Wiley-Interscience Inc., New York, 1977, pp. 348-362.
Fahrenholtz K. E. et al., Octahydrophenanthrene analogs of tetrabenazine, *J. Med. Chem.* 9:304-310, 1967.

(Continued)

*Primary Examiner* — Michael G Hartley
*Assistant Examiner* — Jennifer Lamberski
(74) *Attorney, Agent, or Firm* — Woodcock Washburn, LLP

(57) ABSTRACT

This invention relates to a method of imaging vesicular monoamine transporters and to labeled compounds and pharmaceutical compositions thereof, and methods of making labeled compounds useful in imaging vesicular monoamine transporters. This invention also relates to compounds, and methods of monitoring progression of a disease related to vesicular monoamine transporters.

9 Claims, 10 Drawing Sheets

(56) References Cited

OTHER PUBLICATIONS

Harnden M. R., Short J. H. 2-Thiol-1,3,4,6,7,11b-hexahydro-9,10-dimethoxy-2H-benzo[a]quinolizines. *J. Med. Chem*, 10:1183-1184, 1967.
Pletscher A., Brossi A., Gey K. F. Benzoquinoline derivatives: A new class of monoamine decreasing drugs with psychotropic action, *Rev. Neurobiol.*, 4:275-302, 1962.
Scherman D. et al., Hydrophobicity of the tetrabenazine-binding site of the chromaffin granule monoamine transporter, *Mol. Pharmacol.*, 33:72-77, 1988.
Albin R, Koeppe R., Rapid loss of striatal VMAT2 binding associated with onset of Lewy body dementia, *Mov Disord.*, 2006:21:287-88.
Tatsch K., Can SPET imaging of dopamine uptake sites replace PET imaging in Parkinson's disease?, *Eur J Nucl Med Mol Imaging.*, 2002:29:711-14.
Brooks DJ., Monitoring neuroprotection and restorative therapies in Parkinson's disease with PET, *J. Neural. Transm. Suppl.*, 2000:60:125-37.
Brooks DJ., The early diagnosis of Parkinson's disease, *Ann Neurol.*, 1998:44:S10-S18.
Frey KA. Can SPET imaging of dopamine uptake sites replace PET imaging in Parkinson's disease? Against, *Eur J Nucl Med Mol Imaging*, 2002:29:715-17.
Lee CS et al., In vivo positron emission tomography evidence for compensatory changes in presynaptic dopaminergic nerve terminals in Parkinson's disease, *Ann. Neurol.*, 2000:47:493-503.
Meegalla SK, et al., Specificity of diastereomers of [$^{99m}$Tc]TRODAT-1 as dopamine transporter imaging agents, *J. Med. Chem.*, 1998:41:428-36.
Mozley PD et al., Binding of [$^{99m}$Tc]TRODAT-1 to dopamine transporters in patients with parkinson's disease and in healthy volunteers, *J. Nucl. Med.*, 2000:41:584-89.
Ravina B, et al., "The role of radiotracer imaging in Parkinson disease", *Neurology*, 2005:64:208-15.
Albin RL, et al., "Increased ventral striatal monoaminergic innervation in Tourette syndrome," *Neurology*, 2003:61:310-5.
Kilbourn MR, Effects of dopaminergic drug treatments on in vivo radioligand binding to brain vesicular monoamine transporters, *Nucl Med Biol.*, 1996:23:467-71.
Frey KA, Koeppe RA, Kilbourn MR. Imaging the vesicular monoamine transporter, Adv. Neurol., 2001:86:237-47.
Lee CS, Schulzer M, de la Fuente-Fernandez R, Mak E, Kuramoto L, Sossi V, Ruth TJ, Caine DB, Stoessl AJ., Lack of regional selectivity during the progression of Parkinson disease: implications for pathogenesis, *Arch. Neurol.*, 2004:61:1920-5.
Kilbourn, M.R. et al., Absolute configuration of (+)-alpha-dihydrotetrabenazine, an active metabolite of tetrabenazine, *Chirality*, 1997, 9, 59-62.
Frey, K.A. et al., Presynaptic monoaminergic vesicles in Parkinson's disease and normal aging, Ann Neurol., 1996, 40, 873-884.
Albin RL, Koeppe RA, Bohnen NI, Wernette K, Kilbourn MA, Frey KA. Spared caudal brainstem SERT binding in early Parkinson's disease. 2008 J. Cereb. Blood Flow Metab. 28: 441-444.
Maffei, A. et al., Identification of tissue-restricted transcripts in human islets, Endocrinology, 2004, 145, 4513-4521.
Berge S. M., et al., *Pharmaceutical Salts, J. Pharm. Sci.* 66:1-19 (1977).
Kilbourn M, Sherman P. In vivo binding of (+)-[alpha]-[$^3$H]dihydrotetrabenazine to the vesicular monoamine transporter of rat brain: bolus vs. equilibrium studies, Eur. J. Pharmacol., 1997:331:161-68.
Kilbourn M, Lee L, Borght TV, Jewett D, Frey K. Binding of [alpha]-dihydrotetrabenazine to the vesicular monoamine transporter is stereospecific, *Eur. J Pharmacol.*, 1995:278:249-52.
Lowry OH, Rosebrough NJ, Farr AL, Randall RJ., Protein measurement with Folin phenol reagent, *J. Biol. Chem.*, 1951:193:265-75.
Munson PJ, Rodbard D., Ligand: a versatile computerized approach for characterization of ligand-binding systems, *Anal. Biochem.*, 1980:107:220-39.
Anlauf, M. et al., "Expressions of the Two Isoforms of the Vesicular Monoamine Transporter (VMAT1 and VMAT2) in the Endocrine Pancreas and Pancreatic Endocrine Tumors," J Histochem Cytochem, Aug. 2003, vol. 51, pp. 1027-1040.
Hou, C. et al., "Imaging vesicular monoamine transporter sites with fluoroalkyl derivatives of dihydrotetrabenazine," Neuroimage, Academic Press, Orlando, FL, US, vol. 31, Jan. 1, 2006, p. T14, DOI: DOI:10.1016/J.Neuroimage.2006.04.005 [retrieved on Jan. 1, 2006].
Kobor, J. et al., "Synthesis and stereochemical study of cis- and trans-1-(3'-substituted propyl)benzo[a]quinolizidine" Tetrahedron 1994, 50(16), 4873-86.
Popp, F.D. & Watts, R.F. Synthesis of potential antineoplastic agents. XXVI: 1,3,4,6,7,11b-hexahydro-9,10-dimethoxy-2H-benzo[a]2-quinolizinone derivatives' Journal of Pharmaceutical Sciences 1978, 67(6), 871-3.
Caroon et al., Synthesis and Antihypertensive Activity of a Series of Spiro[1,3,4,6,7,11b-hexahydro-2H-benzo[a] quinolizine-2,5'-oxazolidin-2'-one]s[1], J. Med. Chem., 1983, 26(10), 1426-1433.
Suzuta, "Synthesis of Synthesis of Benzoquinolizine Derivatives I. Synthesis of 3-Dimethylaminoalkyl-9,10-dimethoxy-1,2,3,4,6,7-hexahydro-11b*H*-benzo[a]-quinolizine", Journal of the Pharmaceutical Society of Japan Oct. 1959, 79(10), 1314-1318.
Suzuta, "Synthesis of Benzoquinolizine Derivatives II. Synthesis of 2-Dimethylaminoethyl-3-methyl-9,10-dimethoxy-1,2,3,4,6,7-hexahydro-11b*H*-benzo[a]-quinolizine", Journal of the Pharmaceutical Society of Japan, Oct. 1959, 79(10), 1319-1323.

\* cited by examiner

| Compound | Ki (nM ± SEM) |
|---|---|
| Is" | 0.38 ± 0.06 |
| Is' | 0.15 ± 0.01 |

RADIOLABELED DIHYDROTETRABENAZINE DERIVATIVES AND THEIR USE AS IMAGING AGENTS

STATEMENT REGARDING FEDERALLY-SPONSORED RESEARCH AND DEVELOPMENT

Part of the work performed during development of this invention utilized U.S. Government funds. The U.S. Government has certain rights in this invention under a grant awarded by the National Institutes of Health (EB-002171 and NS-015655).

BACKGROUND OF THE INVENTION

1. Field of the Invention

This invention relates to novel bioactive compounds, methods of diagnostic imaging using radiolabeled compounds, and methods of making radiolabeled compounds.

2. Background Art

Monoamine neuronal systems, i.e. serotonergic, dopaminergic and adrenergic neurotransmitters, have been implicated in various neurological and psychiatric disorders. Different types of therapeutic agents aiming at these neuronal systems, as the pharmacological basis for treatment, are well known. Evaluation of the innervation of these neuronal systems is essential and important for understanding the pathophysiology, and for monitoring progress of patient treatment. New and powerful imaging methods which enable one to assess the living brain in vivo and thereby monitor the effectiveness of drugs and substances that affect brain chemistry have recently been developed. Methods such as positron emission tomography (PET) and single photon emission tomography (SPECT) involve the administration to a patient of radioactive tracer substances comprising a ligand that binds to presynaptic or postsynaptic neuroreceptors in the patient's brain. Emissions (primarily gamma rays which are emitted from the positrons or photons emitted from the radioactive tracer) are measured. These emissions are indicative of the number and degree of occupancy or blocking of the neuroreceptors. The number of neuroreceptors and the degree of occupancy or blocking is calculated utilizing a mathematical model, and compared with an intra-person or inter-person control, to determine the degree of drug response. Further treatment of the patient with drugs can be based upon the comparisons made.

The CNS neuronal systems can take up selective neurotransmitters, such as dopamine, serotonin, norepinephrine etc, from either plasma or from the synaptic cleft. This reuptake process is achieved by a selective transport mechanism based on a specific reuptake receptor on the specific type of presynaptic neuronal terminal. However, once the transmitters are inside the specific type of neuron, a second transporter or reuptake and storage mechanism is responsible for storing and packing the neurotransmitters in vesicles (or granules).

The second transport mechanism, contrary to that for the presynaptic reuptake, is based on a common ATP-dependent transporter which resides on the surface of the vesicles. The second transporters are non-selective and are effective for catecholamines, serotonin and histamine. The neurotransmitters stored in the vesicles are protected from degradation by monoamine oxidases (MAOs) in the cytosol. When neural transmissions are induced by electrical signals, the vesicles in the presynaptic neurons are fused with the membrane and the stored neurotransmitters are released into the synaptic cleft for postsynaptic receptor binding, which leads to further signal transduction.

Reserpine is a natural product which inhibits the monoamine uptake-storage mechanism of amine granules in the synapse. Tetrabenazine, 3-(2-methylpropyl)-9,10-dimethoxy-1,3,4,6,7,11b-hexahydro-2H-benzo[a]quinolizin-2-one (TBZ), is an analog of reserpine which displays a similar biological profile. Due to their ability to deplete monoamines in the CNS, both were used as antipsychotic agents in the 1950's (Cooper J. R., Bloom F. E., Ruth R. H., In *Biochemical Basis of Neurochemistry*, 5th ed., Oxford University Press, New York, 1986, p. 290; Neumeyer J. L., Neuroleptics and Axiolytic Agents, In *Principles of Medicinal Chemistry*, Foye, W. O., ed. Lea and Febiger, Philadelphia, Pa., 1981; Kaiser C., Setler P. E., Antipsychotic Agents, *Burger's Medicinal Chemistry*, 4th Ed. Wolf M. E., ed. Wiley-Interscience, New York, 1981, pp 860-964). The depletion of catecholamines and serotonin in the brain by reserpine is long-lasting and the storage mechanism is irreversibly damaged. Tetrabenazine produces a similar effect; however, the drug effects of TBZ are of a shorter duration and do not cause irreversible damage to neurons (Cooper J. R., et al. In *Biochemical Basis of Neurochemistry*; and Neumeyer J. L. In *Principles of Medicinal Chemistry*). Clinical studies appear to suggest that treatment of patients with TBZ with up to 300 mg daily improved tardive dyskinesia in several trials (Neumeyer J. L.).

Recently, [$^3$H]dihydro-TBZ (2-hydroxy-3-(2-methylpropyl)-9,10-dimethoxy-1,3,4,6,7,11b-hexahydro-2H-benzo[a]quinolizine) has been used as a selective marker for the monoamine transport system in vitro. A detailed review of the use of [$^3$H]dihydro-TBZ and [$^3$H]reserpine as ligands for in vitro investigation of the monoamine transporter of chromaffin granules and CNS synaptic vesicles was published recently (Henry, J. P., Scherman D., Radioligands of the vesicular monoamine transporter and their use as markers of monoamine storage vesicles, (Commentary) *Biochem. Pharmacol.*, 38:2395-2404, 1989). In vitro binding studies of [$^3$H] dihydro-TBZ using membranes of chromaffin granules and brain tissue samples demonstrated a high binding affinity (Kd=2-9 nM) (Darchen F., Masuo Y., Vial M., Rostene W., Scherman D., Quantitative autoradiography of the rat brain vesicular monoamine transporter using the binding of [$^3$H] dihydrotetrabenazine and 7-amino-8-[$^{125}$I]iodoketanserin, *Neurosci.*, 33:341-349, 1989; Meshgin-Azarian S., Chang W., Cugier D. L., Vincent M. S., Near J. A., Distribution of [$^3$H]dihydrotetrabenazine binding in bovine striatal subsynaptic fractions: Enrichment of higher affinity binding in a synaptic vesicle fraction. *J. Neurochem.* 50:824-830, 1988; Near J. A., [$^3$H]Dihydrotetrabenazine binding to bovine striatal subsynaptic vesicles, *Mol. Pharmacol.*, 30:252-257, 1986; Scherman D., Raisman R., Ploska A., Agid Y., [$^3$H] Dihydrotetrabenazine, a new in vitro monoaminergic probe for human brain, *J. Neurochem.*, 50:1131-1136, 1988; Suchi R., Stem-Bach Y., Gabay T., Schuldiner S. Covalent modification of the amine transporter with N,N'-dicyclohexylcarbodiimide, *Biochem.*, 30:6490-6494, 1991).

The regional distribution of the dihydro-TBZ binding sites in brain sections corresponded to the monoamine cell bodies and nerve endings in normal and lesioned brain sections (Masuo Y., Pelaprat D., Scherman D., Rostene W., [$^3$H]Dihydro-tetrabenazine, a new marker for the visualization of dopaminergic denervation in the rat stratum. *Neurosci. Lett.*, 114:45-50, 1990). Various derivatives of TBZ have been reported (Kaiser C. and Setler P. E. In *Burger's Medicinal Chemistry*; Neumeyer J. L., In Principles of Medicinal Chemistry; Clarke F. H., Hill R. T., Koo J., Lopano R. M., Maseda M. A., Smith M., Soled S., VonVeh G., Vlattas I., A series of hexahydro[1,4]oxazino[3,4-a]isoquinolines as potential neuroleptics, *J. Med. Chem.* 21:785-791, 1978; Saner A., Pletscher A., A benzo[a]quinoline derivative with a neuroleptic-like action on cerebral monoamine turnover. *J. Pharmacol. Exp. Ther.* 203:556-563, 1977; Lednicer D., Mitscher L. A. *The Organic Chemistry of Drug Synthesis*, Wiley-Interscience Inc., New York, 1977, pp 349-361; Fahrenholtz K. E., Capomaggi A., Lurie M., Goldberg M. W., Kierstead R. W. Octahydrophenanthrene analogs of tetrabenazine, *J. Med. Chem.* 9:304-310, 1967; Harnden M. R., Short J. H. 2-Thiol-1,3,4,6,7,11b-hexahydro-9,10-dimethoxy-2H-benzo[a]quinolizines. *J. Med. Chem.*, 10:1183-1184, 1967; Tretter J. R., U.S. Pat. No. 3,053,845; Pletscher A., Brossi A., Gey K. F. Benzoquinoline derivatives: A new class of monoamine decreasing drugs with psychotropic action, *Rev. Neurobiol.*, 4:275-302, 1962; Brossi A., Lidlar H., Walter M., Schnider O. 16. Synthesenversuche in der Emetin-Reihe. 1. Mitteilung. 2-Oxo-hydrobenz[a]chiolizine, *Helv. Chim. Acta.*, 41:119-139, 1958). Reduction of the ketone to dihydro-TBZ does not affect the binding affinity. The alkylated alcohol derivatives also displayed high potency. In addition, the acetyl derivative of dihydro-TBZ has also been shown to retain high affinity for the transporter. (Scherman D., Gasnier B., Jaudon P., Henry J. P. Hydrophobicity of the tetrabenazine-binding site of the chromaffin granule monoamine transporter, *Mol. Pharmacol.*, 33:72-77, 1988).

There are two vesicular monoamine transporters (VMAT): VMAT1, found in the adrenal tissue, and VMAT2. When located in the brain, neuronal VMAT2 is an integral part of the mechanism for the vesicular storage of monoamine neurotransmitters in brain neurons. In contrast to the situation at the synaptic membrane, where there are specific transporters for active reuptake of dopamine, serotonin or norepinephrine from the synapse, movement of monoamines (dopamine, serotonin and norepinephrine) from the cytosol to the vesicular lumen is via a common ATP-dependent transporter. Therefore, imaging VMAT2 in the brain provides a measurement reflecting the integrity (total number) of all three monoaminergic neurons (Albin R, Koeppe R., Rapid loss of striatal VMAT2 binding associated with onset of Lewy body dementia, *Mov Disord.*, 2006:21:287-88.) Using VMAT2 as a marker of identified neuronal populations has suggested selective degeneration of projection neurons in Huntington's disease striatum (Frey K A, Koeppe R A, Kilbourn M R., *Adv. Neurol.;* 86:237-47; Bohnen N I, Albin R L, Koeppe R A, Wernette K A, Kilbourn M R, Minoshima S, Frey K A., *J. Cereb Blood Flow Metab.* (in press)).

Parkinson's disease (PD) is a movement disorder characterized by tremor and dyskinesia. Degeneration of nigrostriatal dopamine neurons plays a central role in PD. Currently, development of neuroprotective agents to slow or prevent the progression of this disease is actively being pursued. There is a compelling need for PET (positron emission tomography) and SPECT (single photon emission computer tomography) imaging agents for early diagnosis and monitoring the progression of PD (Tatsch K., Can SPET imaging of dopamine uptake sites replace PET imaging in Parkinson's disease?, For, *Eur J Nucl Med Mol. Imaging.*, 2002:29:711-14.) On the basis of mechanisms of localization, current PET and SPECT imaging agents for PD can be generally divided into three different categories: 1. Enzymatic activity (aromatic amino acid decarboxylase, AADC); 2. Dopamine transporters (DAT); 3. Vesicular monoamine transporters (VMAT2).

The $^{18}$F labeled 6-fluoro-dopa (FDOPA) was the first PET imaging agent for PD and it remains a commonly used PET agent. It is a false substrate for aromatic amino acid decarboxylase (AADC), the first-step of synthesis of dopamine. PET imaging with [$^{18}$F]6-FDOPA provides a glimpse of neuronal function—in situ synthesis of dopamine (or the lack thereof) (Brooks D J., Monitoring neuroprotection and restorative therapies in Parkinson's disease with PET, *J. Neural. Transm. Suppl.*, 2000:60:125-37; Brooks D J., The early diagnosis of Parkinson's disease, *Ann Neurol.*, 1998:44:S10-S18.)

The AADC is not only localized in dopamine neurons, but also in other brain cells. In the brain of PD patients the AADC enzyme is often up-regulated and the peripheral metabolites, O-methylated derivatives, will also be taken up in the brain contributing to background noise. [$^{18}$F]6-FDOPA imaging reflects the loss of neuronal function related to AADC, and may underestimate the degree of neuronal loss due to compensatory changes (Tatsch K., *Eur J Nucl Med Mol Imaging*; Frey K A. Can SPET imaging of dopamine uptake sites replace PET imaging in Parkinson's disease? Against, *Eur J Nucl Med Mol Imaging*, 2002:29:715-17; Lee C S, Samii A, Sossi V, Ruth T J, Schulzer M, Holden J E, Wudel J, Pal P K, de la Fuente-Fernandez R, Calne D B, Stoessl A J., In vivo positron emission tomographic evidence for compensatory changes in presynaptic dopaminergic nerve terminals in Parkinson's disease, *Ann. Neurol.*, 2000:47:493-503).

In the past ten years there have been a plethora of DAT imaging agents, most of which are tropane (or cocaine) derivatives which have varying degrees of affinity to serotonin and norepinephrine transporters (Meegalla S K, Plössl K, Kung M-P, Stevenson D A, Mu M, Kushner S, Liable-Sands L M, Rheingold A L, Kung H F. Specificity of diastereomers of [$^{99m}$Tc]TRODAT-1 as dopamine transporter imaging agents, *J. Med. Chem.*, 1998:41:428-36; Mozley P D, Schneider J S, Acton P D, Plössl K, Stern M B, Siderowf A, Leopold N A, Li P Y, Alavi A, Kung H F, Binding of [$^{99m}$Tc] TRODAT-1 to dopamine transporters in patients with parkinson's disease and in healthy volunteers, *J. Nucl. Med.*, 2000: 41:584-89). A recent report pointed out the deficiencies in imaging PD based on DAT tracers, which highlighted the urgent need for imaging agents that can reliably diagnose and predict the progress of this neurodegenerative disease. (Ravina B, Eidelberg D, Ahlskog J E, Albin R L, Brooks D J, Carbon M, Dhawan V, Feigin A, Fahn S, Guttman M, Gwinn-Hardy K, McFarland H, Innis R, Katz R G, Kieburtz K, Kish S J, Lange N, Langston J W, Marek K, Morin L, Moy C, Murphy D, Oertel W H, Oliver G, Palesch Y, Powers W, Seibyl J, Sethi K D, Shults C W, Sheehy P, Stoessl A J, Holloway R., The role of radiotracer imaging in Parkinson disease, *Neurology*, 2005:64:208-15).

As an alternative, $^{11}$C labeled TBZ (tetrabenazine) derivatives have been successfully developed targeting VMAT2 and tested in humans (Albin R L, Koeppe R A, Bohnen N I, Nichols T E, Meyer P, Wernette K, Minoshima S, Kilbourn M R, Frey K A., Increased ventral striatal monoaminergic innervation in Tourette syndrome, *Neurology*, 2003:61:310-5). Animal data strongly suggested that [$^{11}$C](+)-DTBZ (dihydrotetrabenazine) is less sensitive to drugs affecting dopamine levels in the brain; therefore it reflects more accurately the concentration of viable monoamine neurons. (Kilbourn M R, Frey K A, Vander Borght T, Sherman P S., Effects of dopaminergic drug treatments on in vivo radioligand binding to brain vesicular monoamine transporters, *Nucl Med. Biol.*, 1996:23:467-71; Frey K A, Koeppe R A, Kilbourn M R. Imaging the vesicular monoamine transporter, *Adv. Neurol.*, 2001:86:237-47; Bohnen N I, Albin R L, Koeppe R A, Wernette K A, Kilbourn M R, Minoshima S, Frey K A. Positron emission tomography of monoaminergic vesicular binding in aging and Parkinson disease, *J. Cereb. Blood Flow Metab.*, 2006: in press; Lee C S, Schulzer M, de la Fuente-Fernandez R, Mak E, Kuramoto L, Sossi V, Ruth T J, Calne D B, Stoessl A J., Lack of regional selectivity during the progression of Parkinson disease: implications for pathogenesis, *Arch. Neurol.*, 2004:61:1920-5). Optically resolved isomer, [$^{11}$C](+)-DTBZ (labeled at the 9-MeO position), is an excellent PET tracer for measuring VMAT2 in the brain (Kilbourn M R, Lee L C, Heeg M J, Jewett D M., Absolute configuration of (+)-alpha-dihydrotetrabenazine, an active metabolite of tetrabenazine, *Chirality*, 1997:9:59-62; Frey K A, Koeppe R A, Kilbourn M R, Vander Borght T M, Albin R L, Gilman S, Kuhl D E., Presynaptic monoaminergic vesicles in Parkinson's disease and normal aging; *Ann. Neurol.* 1996:40:873-84).

Vesicular monoamine transporters (VMAT2) are also expressed in beta cells in the pancreas. The total number of binding sites for VMAT2 in the human pancreas has been determined. The $B_{max}$=0.2 nM which translates to 12 fmol/mg of protein in beta cells. There are about 1,000,000 beta cells in human pancreas (Maffei, A, Z Liu, P Witkowski, et al. "Identification of tissue-restricted transcripts in human islets." *Endocrinology* 145:4513, 2004). Insufficient beta cell mass (BCM) is a pathophysiological state of both type 1 (T1D) and type 2 (T2D) diabetes. Millions of Americans suffer from diabetes. In addition to this, many more millions have prediabetes, a condition that significantly increases the risk of developing T2D, heart disease and stroke. Diabetes is a leading cause of both acquired blindness and kidney failure in adults and is a major risk factor for both heart disease and stroke. Diabetes thus represents a major and fast growing public health burden.

Diabetes mellitus is a spectrum of disorders that all share a common abnormality of elevated blood glucose levels. Although the initial causes of this abnormality are varied (including autoimmunity, genetic risk factors, obesity, pregnancy, drugs, etc.) the common end result is a relative insulin insufficiency, i.e. the pancreatic beta cells do not produce enough insulin to meet metabolic demands (Olefsky, 2001). The two most common types of diabetes are Type I diabetes (T1D) and Type 2 diabetes (T2D).

T1D usually occurs in children or young adults and accounts for less than 10% of all cases of diabetes. T1D is caused by autoimmune destruction of beta cells leading to failure of insulin secretion. This process may take years to manifest, and during the preclinical stage autoimmune antibodies directed against beta cells can be detected in affected patients. Thus in early stages of the disease immune modulation may play an important role in treatment, while in later stages treatment will require replacement of beta cells either through regenerative or transplantation strategies.

T2D is a heterogeneous polygenic disorder that accounts for approximately 90% of all cases of diabetes. In addition to genetic risk factors, obesity, lack of physical activity and aging are important risk factors for T2D. T2D is characterized by insulin resistance, a defect which is present for years in the preclinical (prediabetes) state. This insulin resistance leads to compensatory increases in insulin production by beta cells in prediabetics. Eventually, in some patients, beta cell function then declines, leading to relative insulin insufficiency (Butler et al., 2003). Indeed, autopsy series reveal that BCM is reduced by 50-60% in T2D patients as compared to controls (reviewed in Porte and Kahn, 2001; Prentki and Nolan, 2006). This loss of beta cells may be a key step in the pathogenesis of T2D diabetes since a longitudinal study in Pima Indians suggested that beta cell failure rather than insulin resistance was the primary determinant of progression from prediabetes to diabetes (Weyer et al, 1999). Thus in T2D, insulin resistance superimposed on beta cell failure and impaired insulin secretion lead to decompensated hyperglycemia and diabetes. Disease modifying treatments for T2D must target both beta cell failure and insulin resistance in order to be most effective (Olefsky, 2001).

BRIEF SUMMARY OF THE INVENTION

The present invention provides novel compounds of Formulae I and II (including those of Formulae I' and II') that are useful for imaging vesicular monoamine transporters.

In one aspect, the compounds are useful PET imaging agents.

In another aspect, the compounds are useful SPECT imaging agents.

The present invention also provides diagnostic compositions comprising a radiolabeled compound of Formulae I and II (including those of Formulae I' and II') and a pharmaceutically acceptable carrier or diluent.

The invention further provides a method of imaging vesicular monoamine transporters, the method comprising introducing into a patient a detectable quantity of a labeled compound of Formulae I and II (including those of Formulae I' and II') or a pharmaceutically acceptable salt, ester, amide, or prodrug thereof.

A further aspect of this invention is directed to methods and intermediates useful for synthesizing the vesicular monoamine transporter imaging compounds of Formulae I and II (including those of Formulae I' and II') described herein.

The invention also is directed to a method of monitoring the status, quantity, change of, or progression of a disorder or disease related to vesicular monoamine transporters.

DETAILED DESCRIPTION OF THE INVENTION

Figure 1:
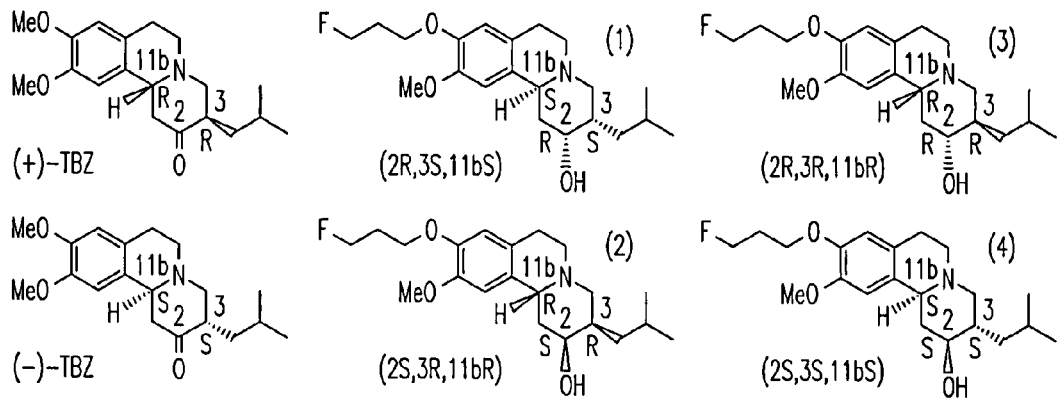
FIG. 1 shows the separation of stereoisomers of FP-(±)-DTBZ (also referred to herein as "6b" or "(±)-6b") on a chiral AD column with hexanes/isopropanol (9/1) as the eluting solvent (flow rate of 1 ml/min). The ratio of two major stereoisomers (peaks 3 & 4) to the minor peaks (peaks 1 & 2) is 5:1. The optical resolution of FP-(+)-DTBZ (2R, 3R, 11bR) (also referred to herein as "(+)-6b") reached 98% (shown as peak 3) and the isomer FP-(−)-DTBZ showed a major peak (peak 4, 90%) with a contaminant peak (peak 1, 10%).
Figure 1:
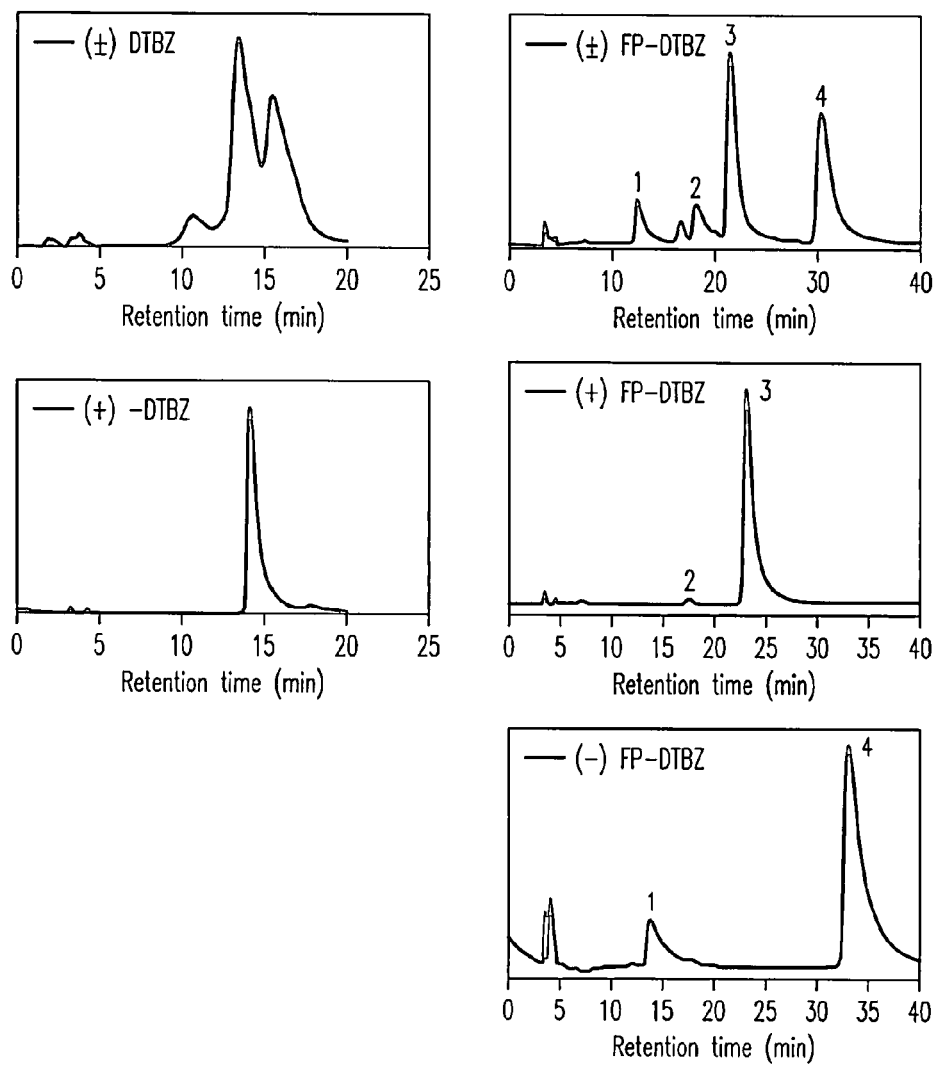

A first aspect of the present invention is directed to compounds of the following Formula I:

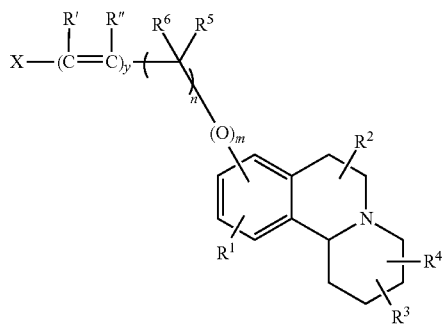

or a pharmaceutically acceptable salt thereof, wherein: n is an integer from 0 to 10; m is 1 or 0; y is 1 or 0; X is halogen; $R^1$ and $R^2$ are independently hydrogen, $C_{1-5}$ alkyl, amino($C_{1-5}$) alkyl, halo($C_{1-4}$)alkyl, mono- or di-($C_{1-5}$)alkylamino, haloarylalkyl, $C_{1-5}$ alkoxy; $R^3$ is keto

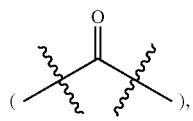 [SMILES: *C(*)=O]

an epoxide ring

hydroxy, hydrogen, amino($C_{1-5}$)alkyl, mono- or di-($C_{1-5}$) alkylamino, $C_{1-5}$ alkoxy or $C_{1-4}$ alkyl; $R^4$ is hydrogen, $C_{1-10}$ alkyl, amino($C_{1-5}$)alkyl, mono- or di-($C_{1-5}$)alkylamino; and when present, R', R'', $R^5$ and $R^6$ are independently hydrogen, hydroxy, hydroxy($C_{1-5}$)alkyl or $C_{1-5}$ alkyl.

Useful values of X include any halogen. In this embodiment, it is preferable that the halogen is a radiohalogen. Radiohalogens include $^{125}$I, $^{123}$I, $^{131}$I, $^{18}$F, $^{19}$F, $^{76}$Br and $^{77}$Br. More preferably, X is $^{18}$F or $^{123}$I. In one embodiment, the most preferred compounds of Formula I are those compounds where X is $^{18}$F. These compounds are particularly useful for PET imaging. In another embodiment, the most preferred compounds of Formula I are those compounds where X is $^{125}$I, $^{123}$I, $^{131}$I, particularly $^{123}$I. These compounds are particularly useful for SPECT imaging.

Useful values of $R^3$ include those listed above. Preferably, $R^3$ is keto

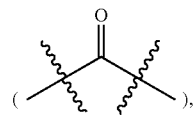

epoxide ring

or hydroxy. Most preferably, $R^3$ is hydroxy. When $R^3$ is keto

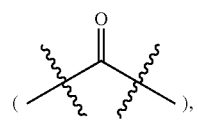 [SMILES: *C(*)=O]

the O is double bonded to any one of the available ring carbons. Thus, for example, these compounds can have the following ring scaffold, which contains substituents as described herein:

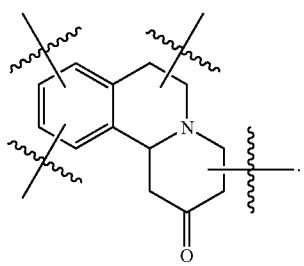

When $R^3$ is an epoxide ring

the O is bonded to any one of the available ring carbons as well as a methylene group which is also bonded to the same ring carbon to form the 3-membered ring system. Thus, for example, these compounds can have the following ring scaffold, which contains substituents as described herein (showing preferred stereochemistry):

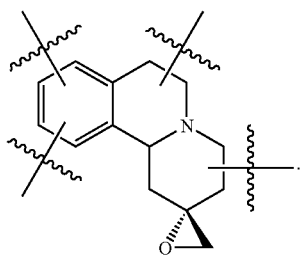

Useful values of $R^4$ include all those listed above. Preferred values include $C_{1-10}$ alkyl, amino($C_{1-5}$)alkyl and mono- or di-($C_{1-5}$)alkylamino. Most preferably, $R^4$ is $C_{1-5}$ alkyl, and more specifically isobutyl.

Useful values of $R^1$ include all those listed above. Preferred values include amino($C_{1-5}$)alkyl, mono- or di-($C_{1-5}$)alkylamino and $C_{1-5}$ alkoxy. More preferably, $R^1$ is $C_{1-5}$ alkoxy. Most preferably, $R^1$ is methoxy.

Useful values of $R^2$ include all those listed above. In preferred embodiments, $R^2$ is hydrogen.

Useful values of $R^5$ and $R^6$ include hydroxy, hydrogen and $C_{1-5}$ alkyl. The number of occurrences of $R^5$ and $R^6$ depends on the value of n. When $R^5$ and $R^6$ occur more than once, each occurrence is independent of another. In preferred embodiments, at least one of $R^5$ and $R^6$ is hydrogen. Most preferably, $R^5$ and $R^6$ are both hydrogen in every occurrence.

Useful values of m and n are all those listed above. The value of m, in each instance, is independent relative to the value of n. In Formula I compounds, preferred values of n are integers from 1 to 6. More preferably, n is an integer from 1 to 4. Most preferably, n is 2, 3 or 4. The useful values of m include 1 or 0. However, in one preferred embodiment, when m is 0, n is also 0.

Useful values of y include 1 and 0. Preferably, y is 0.

In a particular embodiment, the present invention is directed to compounds of Formula I, that have the following stereochemical structure, Formula I':

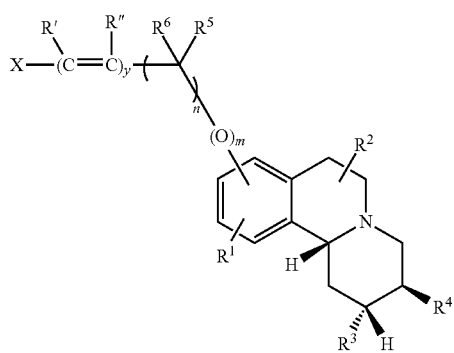

or a pharmaceutically acceptable salt thereof, wherein: n is an integer from 0 to 10; m is 1 or 0; y is 1 or 0; X is halogen; $R^1$ and $R^2$ are independently hydrogen, $C_{1-5}$ alkyl, amino($C_{1-5}$)alkyl, halo($C_{1-4}$)alkyl, mono- or di-($C_{1-5}$)alkylamino, haloarylalkyl, $C_{1-5}$ alkoxy; $R^3$ is hydroxy, keto, an epoxide ring

hydrogen, amino($C_{1-5}$)alkyl, mono- or di-($C_{1-5}$)alkylamino, $C_{1-5}$ alkoxy or $C_{1-4}$ alkyl; $R^4$ is hydrogen, $C_{1-10}$ alkyl, amino($C_{1-5}$)alkyl, mono- or di-($C_{1-5}$)alkylamino; and when present, R', R'', $R^5$ and $R^6$ are independently hydrogen, hydroxy, hydroxy($C_{1-5}$)alkyl or $C_{1-5}$ alkyl.

Useful values of X include any halogen. In this embodiment, it is preferable that the halogen is a radiohalogen. Radiohalogens include $^{125}I$, $^{123}I$, $^{131}I$, $^{18}F$, $^{19}F$, $^{76}Br$ and $^{77}Br$. More preferably, X is $^{18}F$ or $^{123}I$. In one embodiment, the most preferred compounds of Formula I' are those compounds where X is $^{18}F$. These compounds are particularly useful for PET imaging. In another embodiment, the most preferred compounds of Formula I' are those compounds where X is $^{125}I$, $^{123}I$, $^{131}I$, particularly $^{123}I$. These compounds are particularly useful for SPECT imaging.

Useful values of $R^3$ include those listed above. Most preferably, $R^3$ is keto, hydroxy or an epoxide ring

Useful values of $R^4$ include all those listed above. Preferred values include $C_{1-10}$ alkyl, amino($C_{1-5}$)alkyl and mono- or di-($C_{1-5}$)alkylamino. Most preferably, $R^4$ is $C_{1-5}$ alkyl, and more specifically isobutyl.

Useful values of $R^1$ include all those listed above. Preferred values include amino($C_{1-5}$)alkyl, mono- or di-($C_{1-5}$)alkylamino and $C_{1-5}$ alkoxy. More preferably, $R^1$ is $C_{1-5}$ alkoxy. Most preferably, $R^1$ is methoxy.

Useful values of $R^2$ include all those listed above. In preferred embodiments, $R^2$ is hydrogen.

Useful values of $R^5$ and $R^6$ include hydroxy, hydrogen and $C_{1-5}$ alkyl. The number of occurrences of $R^5$ and $R^6$ depends on the value of n. When $R^5$ and $R^6$ occur more than once, each occurrence is independent of another. In preferred embodiments, at least one of $R^5$ and $R^6$ is hydrogen. Most preferably, $R^5$ and $R^6$ are both hydrogen in every occurrence.

Useful values of m and n are all those listed above. The value of m, in each instance, is independent relative to the value of n. In Formula I' compounds, preferred values of n are integers from 1 to 6. More preferably n is an integer from 1 to 5, especially 1 to 4. However, most preferably, n is 2, 3 or 4. The useful values of m include 1 or 0. However, in one preferred embodiment, when m is 0, n is also 0.

Useful values of y include 1 and 0. Preferably, y is 0.

Preferred compounds of Formula I or I' include those with the following structures:

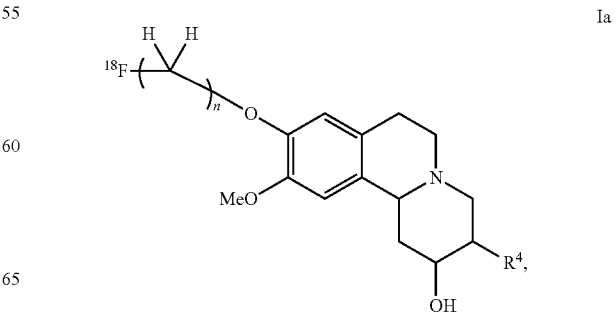

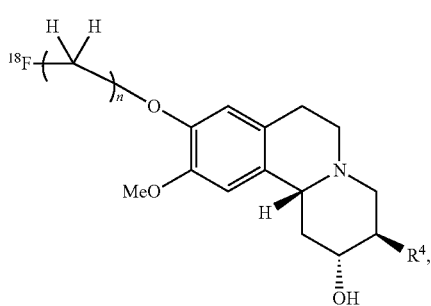
Ib

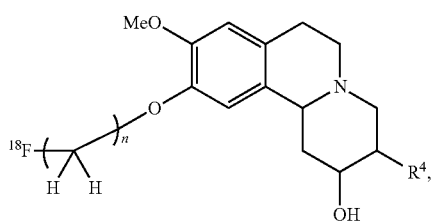
Ic

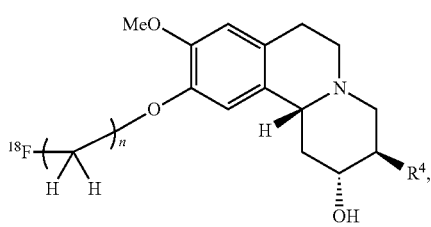
Id wherein, in compounds Ia, Ib, Ic and Id, n is an integer from 1 to 6, and $R^4$ is $C_{1-10}$ alkyl, preferably $C_{1-4}$ alkyl, most preferably isobutyl;

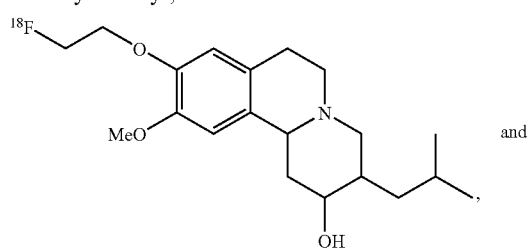
Ie and

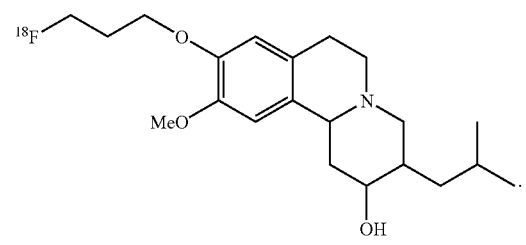
If

Preferred compounds of Formula I or I', wherein y is 0, m is 0 and n is 0 include those with the following structures:

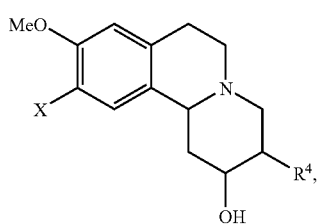
Ig

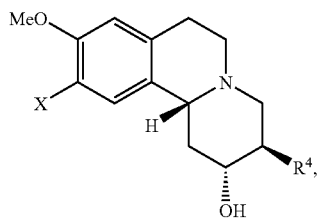
Ih

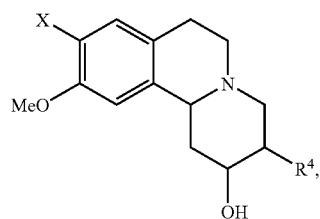
Ii

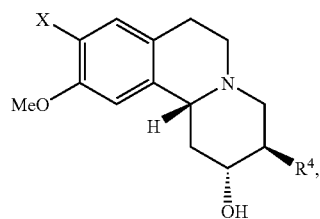
Ij wherein, in compounds Ig, Ih, Ii and Ij, X is $^{18}F$ or $^{123}I$, and $R^4$ is $C_{1-10}$ alkyl, preferably $C_{1-4}$ alky, most preferably isobutyl;

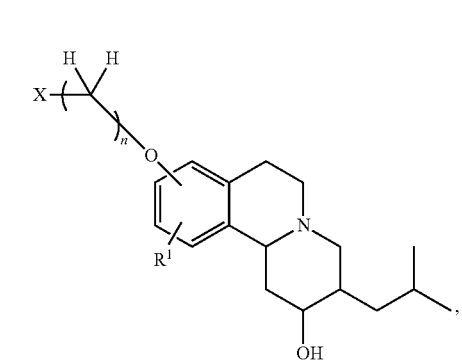
Ik

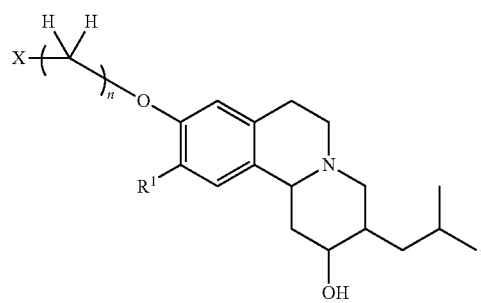
Il wherein, n is an integer from 1 to 6; X is $^{18}F$ or $^{123}I$; and $R^1$ is $C_{1-5}$ alkoxy;

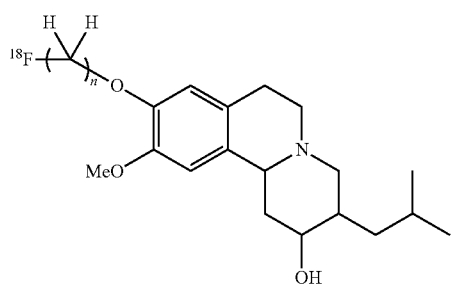

Im wherein n is 2, 3 or 4;

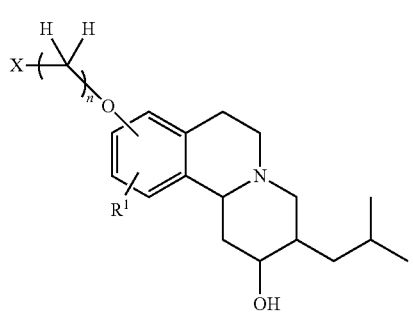

In wherein, n is an integer from 1 to 5; X is $^{18}$F or $^{123}$I; and R$^1$ is C$_{1-5}$ alkoxy;

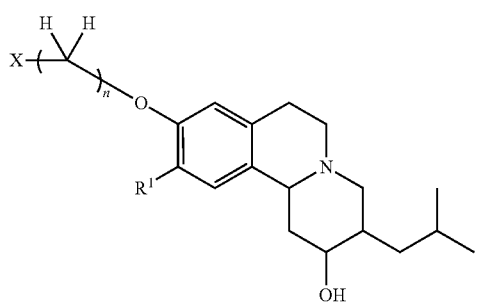

Io wherein, n is an integer from 1 to 4; X is $^{18}$F or $^{123}$I; and R$^1$ is C$_{1-5}$ alkoxy; and

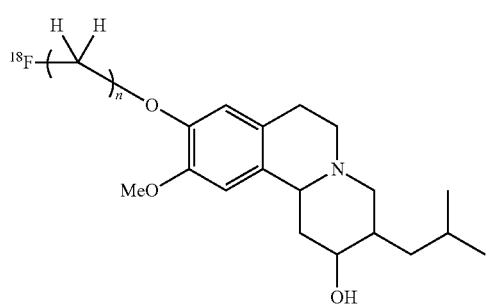

Ip wherein, n is 2, 3 or 4.

Other stereospecific structures that are preferred include:

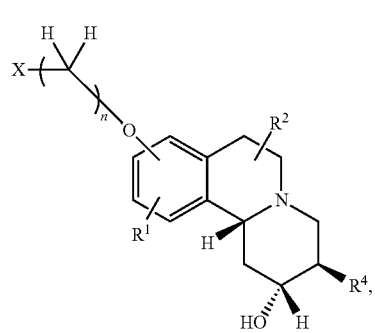

Iq

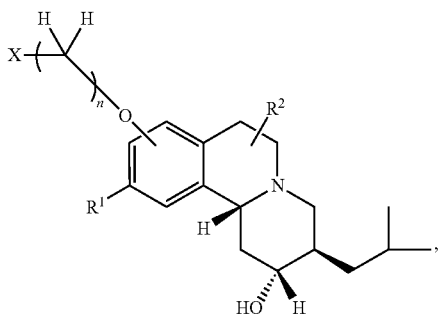

Ir wherein, n is an integer from 1 to 5; X is $^{18}$F or $^{123}$I, R$^4$ is C$_{1-4}$ alkyl and R$^1$ is C$_{1-5}$ alkoxy;

Is wherein, n is an integer from 1 to 5; X is $^{18}$F or $^{123}$I, R$^4$ is C$_{1-4}$ alkyl and R$^1$ is C$_{1-5}$ alkoxy;

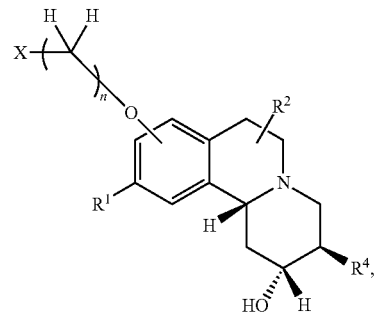

It wherein, n is an integer from 1 to 4, X is $^{18}$F or $^{123}$I, R$^4$ is C$_{1-4}$ alkyl and R$^1$ is C$_{1-5}$ alkoxy;

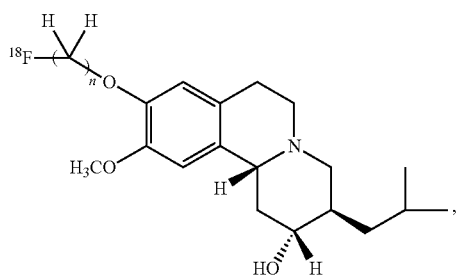

Iu wherein, n is 2 or 3; and

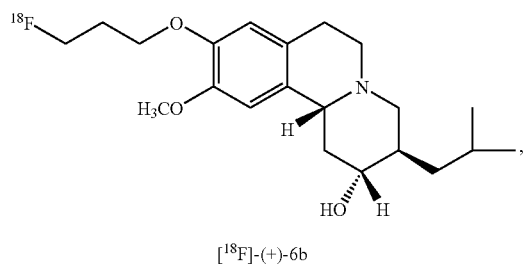 [SMILES: COc1cc2c(cc1OCCC[18F])CCN1C[C@@H](CC(C)C)[C@H](O)C[C@H]21]

[$^{18}$F]-(+)-6b or a pharmaceutically acceptable salt thereof.

Alternatively where $R^3$ is an epoxide ring

, the preferred compounds of Formula I or I' include those with the following structures:

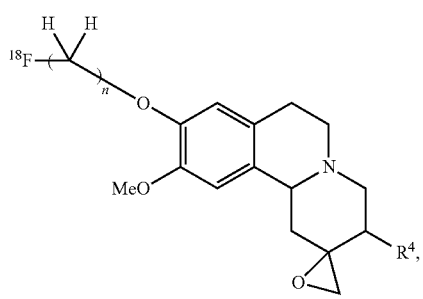

Ia'

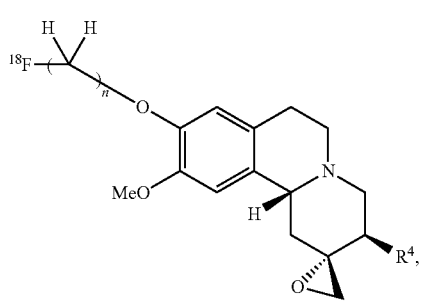

Ib'

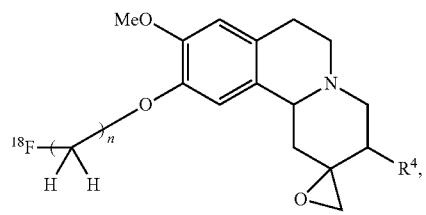

Ic'

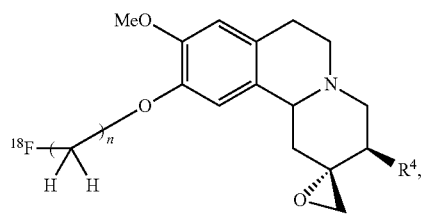

Id' wherein, in compounds Ia, Ib, Ic and Id, n is an integer from 1 to 6, and $R^4$ is $C_{1-10}$ alkyl, preferably $C_{1-4}$ alkyl, most preferably isobutyl;

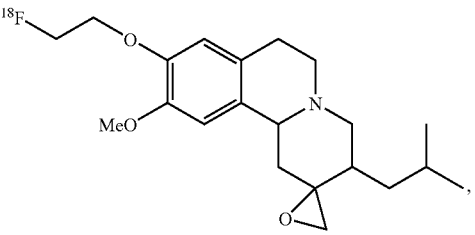

Ie'

, and

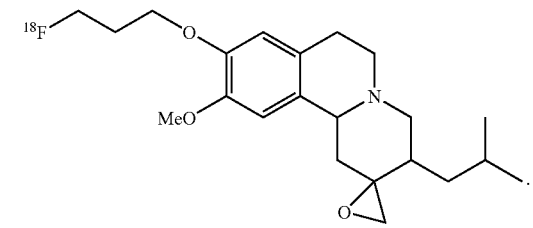

If'

.

Preferred compounds of Formula I or I', wherein y is 0, m is 0 and n is 0 include those with the following structures:

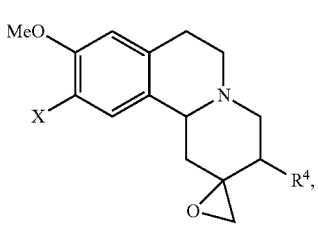

Ig'

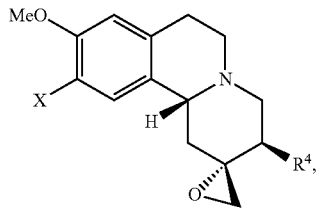
Ih'

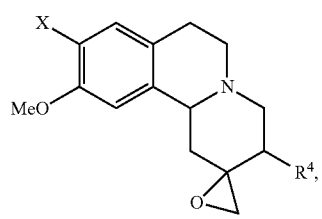
Ii'

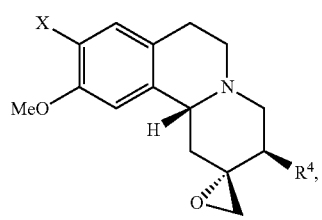
Ij' wherein, in compounds Ig, Ih, Ii and Ij, X is $^{18}$F or $^{123}$I, and R$^4$ is C$_{1-10}$ alkyl, preferably C$_{1-4}$ alky, most preferably isobutyl;

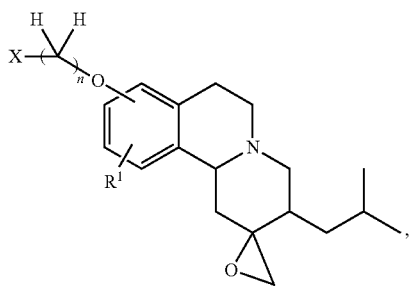
Ik'

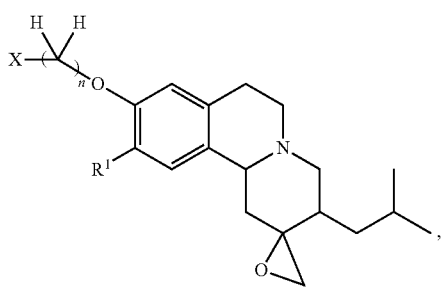
Il' wherein, n is an integer from 1 to 6, preferably 1 to 5 and more preferably 1 to 4; X is $^{18}$F or $^{123}$I; and R$^1$ is C$_{1-5}$ alkoxy;

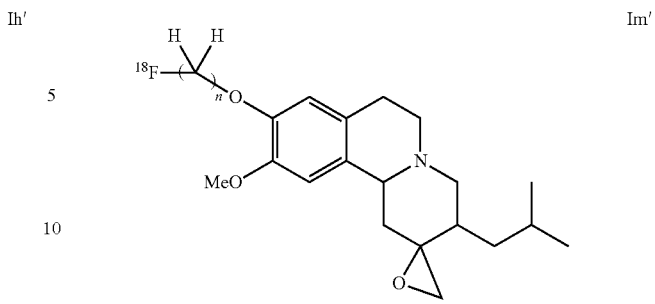
Im' wherein n is 2, 3 or 4.

Other stereospecific structures that are preferred include:

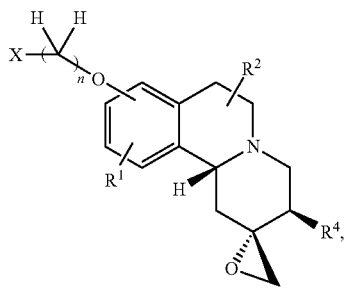
In'

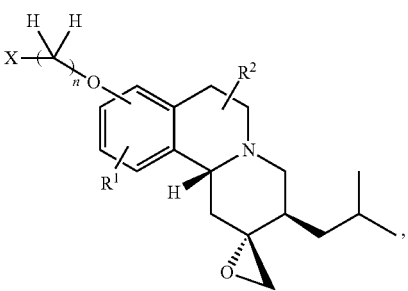
Io' wherein, n is an integer from 1 to 5; X is $^{18}$F or $^{121}$I, R$^4$ is C$_{1-4}$ alkyl and R$^1$ is C$_{1-5}$ alkoxy;

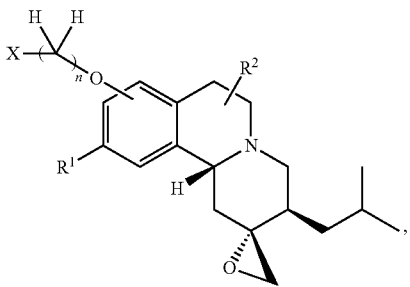
Ip'

-continued

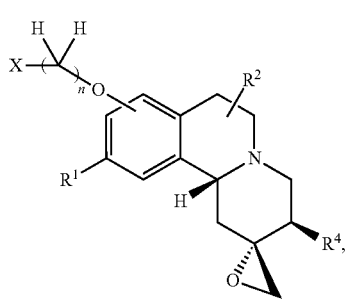

Iq' wherein, n is an integer from 1 to 4, X is $^{18}F$ or $^{123}I$, $R^4$ is $C_{1-4}$ alkyl and $R^1$ is $C_{1-5}$ alkoxy;

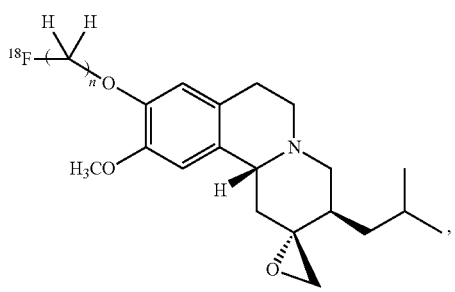

Ir' wherein, n is 2 or 3; and

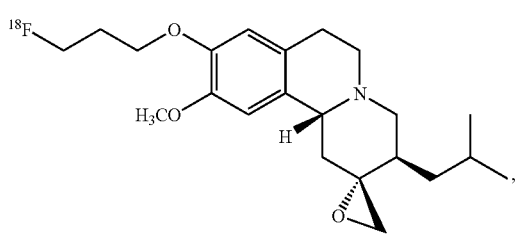

Is' or a pharmaceutically acceptable salt thereof.

In compounds where $R^3$ is a is keto

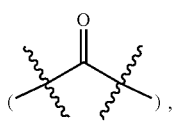

the O is double bonded to any one of the available ring carbons, for example:

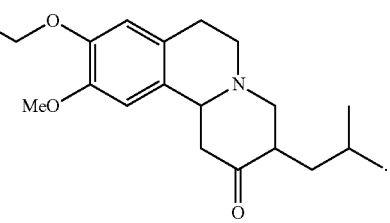

Is"

In another aspect, the present invention is directed to compounds of the following Formula II:

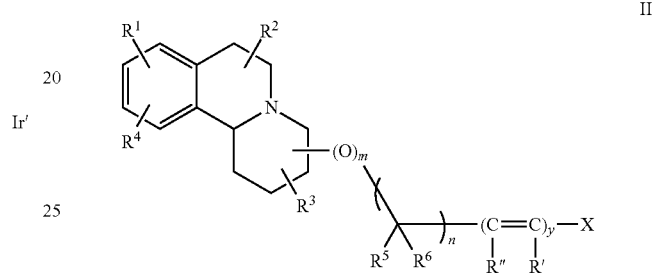

II or a pharmaceutically acceptable salt thereof, wherein: n is an integer from 1 to 10; m is 1 or 0; y is 1 or 0; X is halogen; R, $R^2$ and $R^4$ are independently hydrogen, $C_{1-5}$ alkyl, amino $(C_{1-5})$alkyl, halo$(C_{1-4})$alkyl, mono- or di-$(C_{1-5})$alkylamino, haloarylalkyl, $C_{1-5}$ alkoxy; $R^3$ is keto

an epoxide ring

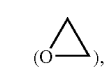

hydroxy, hydrogen, amino$(C_{1-5})$alkyl, mono- or di-$(C_{1-5})$ alkylamino, $C_{1-5}$ alkoxy or $C_{1-4}$ alkyl; and when present, R', R", $R^5$ and $R^6$ are independently hydrogen, hydroxy, hydroxy $(C_{1-5})$alkyl or $C_{1-5}$ alkyl.

Useful values of X include halogen. In this embodiment, it is preferable that the halogen is a radiohalogen. Radiohalogens include $^{125}I$, $^{123}I$, $^{131}I$, $^{18}F$, $^{19}F$, $^{76}Br$ and $^{77}Br$. More preferably, X is $^{18}F$ or $^{123}I$. In one embodiment, the most preferred compounds of Formula II are those compounds where X is $^{18}F$ and y is 0. These compounds are particularly useful for PET imaging. In another embodiment, the most preferred compounds of Formula II are those compounds where X is $^{125}I$, $^{123}I$, $^{131}I$, particularly $^{123}I$, and y is 1. These compounds are particularly useful for SPECT imaging.

Useful values of $R^3$ include those listed above. Preferably, $R^3$ is keto

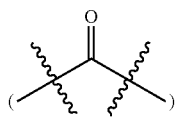 [SMILES: *C(*)=O]

hydroxyl or an epoxide ring

Most preferably, $R^3$ is hydroxy. When $R^3$ is keto

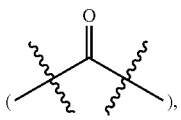 [SMILES: *C(*)=O]

the O is double bonded to any one of the available ring carbons. Thus, for example, these compounds can have the following ring scaffold, which contains substituents as described herein:

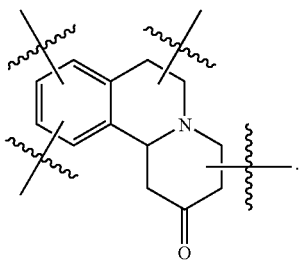

When $R^3$ is an epoxide ring

the O is bonded to any one of the available ring carbons as well as a methylene group which is also bonded to the same ring carbon to form the 3-membered ring system. Thus, for example, these compounds can have the following ring scaffold, which contains substituents as described herein:

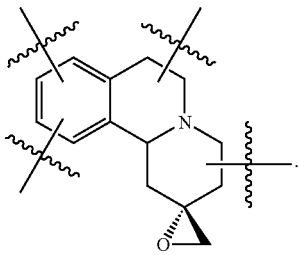

Useful values of $R^4$ include all those listed above. Preferred values include amino($C_{1-5}$)alkyl, mono- or di-($C_{1-5}$)alkylamino and $C_{1-5}$ alkoxy. More preferably, $R^4$ is $C_{1-5}$alkoxy. Most preferably, $R^4$ is methoxy.

Useful values of $R^1$ include all those listed above. Preferred values include amino($C_{1-5}$)alkyl, mono- or di-($C_{1-5}$)alkylamino and $C_{1-5}$ alkoxy. More preferably, $R^1$ is $C_{1-5}$ alkoxy. Most preferably, $R^1$ is methoxy.

Useful values of $R^2$ include all those listed above. In preferred embodiments, $R^2$ is hydrogen.

Useful values of R', R", $R^5$ and $R^6$ include hydroxy, hydrogen and $C_{1-5}$ alkyl. The number of occurrences of $R^5$ and $R^6$ depends on the value of n. When $R^5$ and $R^6$ occur more than once, each occurrence is independent of another. In preferred embodiments, at least one of $R^5$ and $R^6$ is hydrogen. Most preferably, $R^5$ and $R^6$ are both hydrogen in every occurrence.

Useful values of m and n are all those listed above. The value of m, in each instance, is independent relative to the value of n. In Formula II compounds, preferred values of n include an integer from 1 to 10. More preferably, n is an integer from 2 to 7. Most preferably, n is from 3 to 6. The useful values of m include 1 or 0. In a preferred embodiment, m is 0.

Useful values of y include 1 and 0.

In a particular embodiment, the present invention is directed to compounds of Formula II, that have the following stereochemical structure, Formula II'

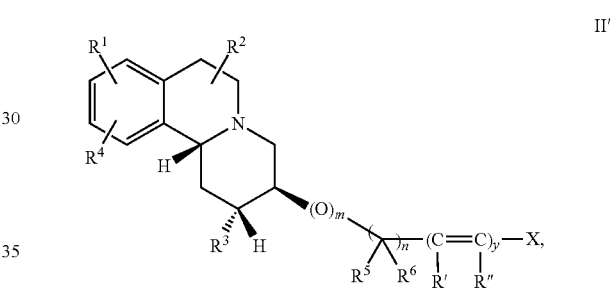

II' or a pharmaceutically acceptable salt thereof, wherein: n is an integer from 1 to 10; m is 1 or 0; y is 1 or 0; X is halogen; R, $R^2$ and $R^4$ are independently hydrogen, $C_{1-5}$ alkyl, amino($C_{1-5}$)alkyl, halo($C_{1-4}$)alkyl, mono- or di-($C_{1-5}$)alkylamino, haloarylalkyl, $C_{1-5}$ alkoxy; $R^3$ is hydroxy, hydrogen, amino($C_{1-5}$)alkyl, mono- or di-($C_{1-5}$)alkylamino, $C_{1-5}$ alkoxy or $C_{1-4}$ alkyl; and when present, R', R", $R^5$ and $R^6$ are independently hydrogen, hydroxy, hydroxy($C_{1-5}$)alkyl or $C_{1-5}$ alkyl.

Useful values of X include halogen. In this embodiment, it is preferable that the halogen is a radiohalogen. Radiohalogens include $^{125}$I, $^{123}$I, $^{131}$I, $^{18}$F, $^{19}$F, $^{76}$Br and $^{77}$Br. More preferably, X is $^{18}$F or $^{123}$I. In one embodiment, the most preferred compounds of Formula II' are those compounds where X is $^{18}$F and y is 0. These compounds are particularly useful for PET imaging. In another embodiment, the most preferred compounds of Formula II' are those compounds where X is $^{125}$I, $^{123}$I, $^{131}$I, particularly $^{123}$I, and y is 1. These compounds are particularly useful for SPECT imaging.

Useful values of $R^3$ include those listed above. Most preferably, $R^3$ is keto, hydroxy or an epoxide ring

Useful values of $R^4$ include all those listed above. Preferred values include amino($C_{1-5}$)alkyl, mono- or di-($C_{1-5}$)alkylamino and $C_{1-5}$ alkoxy. More preferably, $R^4$ is $C_{1-5}$ alkoxy. Most preferably, $R^4$ is methoxy.

Useful values of $R^1$ include all those listed above. Preferred values include amino($C_{1-5}$)alkyl, mono- or di-($C_{1-5}$)alkylamino and $C_{1-5}$ alkoxy. More preferably, $R^1$ is $C_{1-5}$ alkoxy. Most preferably, $R^1$ is methoxy.

Useful values of $R^2$ include all those listed above. In preferred embodiments, $R^2$ is hydrogen.

Useful values of R', R", $R^5$ and $R^6$ include hydroxy, hydrogen and $C_{1-5}$ alkyl. The number of occurrences of $R^5$ and $R^6$ depends on the value of n. When $R^5$ and $R^6$ occur more than once, each occurrence is independent of another. In preferred embodiments, at least one of $R^5$ and $R^6$ is hydrogen. Most preferably, $R^5$ and $R^6$ are both hydrogen in every occurrence.

Useful values of m and n are all those listed above. The value of m, in each instance, is independent relative to the value of n. In Formula II' compounds, preferred values of n include an integer from 1 to 10. More preferably, n is an integer from 2 to 7. Most preferably, n is from 3 to 6. The useful values of m include 1 or 0. In a preferred embodiment, m is 0.

Useful values of y include 1 and 0.

Preferred compounds of Formula II include those with the following general structure, wherein m is 0 and y is 1:

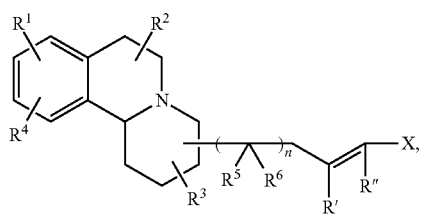

IIa wherein, $R^1$, $R^2$, $R^3$, $R^4$, $R^5$, $R^6$, R', R" are as described above under Formula II, and X is Br or I (including their radioisotopes). Preferably, $R^1$ and $R^4$ are $C_{1-5}$ alkoxy, most preferably methoxy; preferably $R^2$ is hydrogen; preferably $R^3$ is hydroxy; preferably n is an integer from 1 to 10, more preferably from 2 to 7, and most preferably 3 to 6; preferably R' and R" are hydrogen; and X is a radiolabeled halogen.

Preferred compounds of Formula II include those with the following structures:

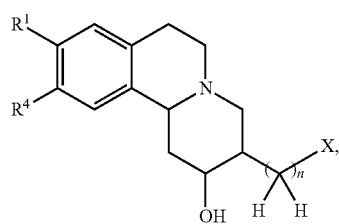

IIb wherein, $R^1$ and $R^4$ are $C_{1-5}$ alkoxy, preferably methoxy; n is an integer from 1 to 10 preferably 2 to 7, and most preferably 3 to 6; and X is $^{18}$F. Other preferred compounds of Formula II or II' include those with the following structures:

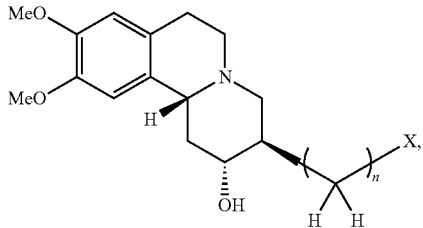

IIc

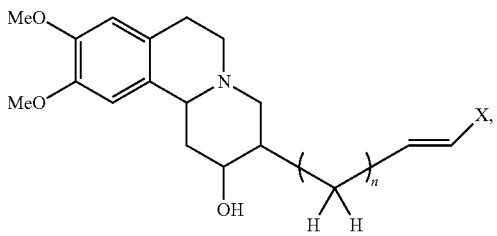

IId

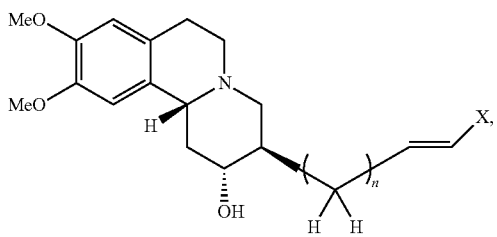

IIe wherein, in compounds IIc, IId, and IIe, n is an integer from 1 to 10, preferably 2 to 7, most preferably 3 to 6, and X is $^{18}$F or $^{123}$I.

Other stereospecific structures that are preferred include:

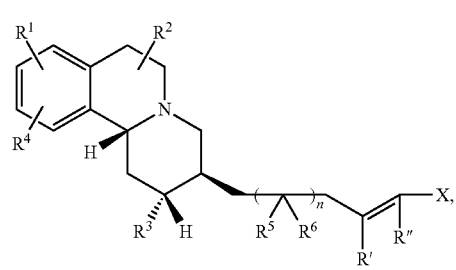

IIf wherein, R, R, $R^3$, R, $R^5$, $R^6$, R' and R" are as described above, n is from 2 to 7, and X

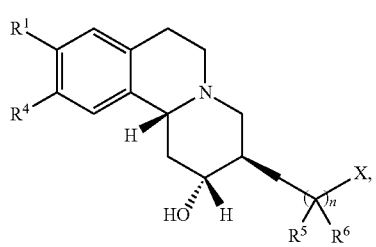

IIg wherein, n is from 2 to 7, $R^1$ and $R^4$ are independently $C_{1-5}$ alkoxy and X is $^{18}$F;

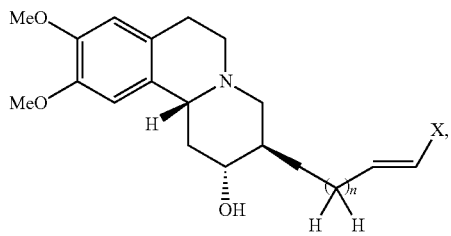

wherein, n is an integer from 1 to 10, and X is $^{123}$I; and

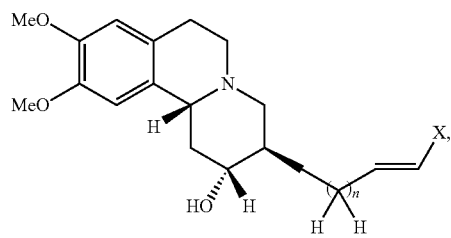

wherein, n is an integer from 1 to 10, and X is $^{18}$F; or a pharmaceutically acceptable salt thereof.

In another embodiment, the present invention is directed to a compound of Formula I' or II' that is substantially purified from its stereoisomers. Substantially purified means that the compound of Formula I' or II' is present at no less than about 75% purity. In a preferred embodiment, the compound of Formula I' or II' is present at no less than about 85% purity. Most preferably, the compound of Formula I' or II' is present at no less than about 95% purity.

It is also to be understood that the present invention is considered to include stereoisomers as well as optical isomers, e.g. mixtures of enantiomers as well as individual enantiomers and diastereomers, which arise as a consequence of structural asymmetry in selected compounds of the present invention.

The compounds of Formulae I and II (including those of Formulae I' and II') may also be solvated, especially hydrated. Hydration may occur during manufacturing of the compounds or compositions comprising the compounds, or the hydration may occur over time due to the hygroscopic nature of the compounds. In addition, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

When any variable occurs more than one time in any constituent or in Formula I or II (including those of Formulae I' and II'), its definition on each occurrence is independent of its definition at every other occurrence. Also combinations of substituents and/or variables are permissible only if such combinations result in stable compounds.

Another aspect of this invention is related to methods of preparing compounds of Formulae I and II (including those of Formulae I' and II').

In another aspect, the invention is directed to methods of imaging vesicular monoamine transporters. Specifically, the compounds described herein are useful for imaging VMAT-2. The imaging of vesicular monoamine transporters can also be carried out quantitatively so that the amount, or change in amount of vesicular monoamine transporters can be determined. This method of quantitative imaging can be used to diagnose or track the progress of a disease. This method further provides for the ability to image the location of transporters, and also to determine any change in the transporters, reflected by a change in the images yielded by the methods.

For example, it is desirable to locate vesicular monoamine transporters in the brain in order to diagnose or track the progress of a vesicular monoamine transporter related disease in a patient, such as, but not limited to, Huntington's and Parkinson's. In another non-limiting example, it is desirable to locate vesicular monoamine transporters in the pancreas in order to diagnose or track the progress of a vesicular monoamine disease in a patient. Such diseases include but are not limited to diabetes. The invention provides a method of tracking the progress of a condition, disorder or disease by comparing the quantity, density and/or location of vesicular monoamine transporters over the course of time.

In one aspect, the methods of imaging are directed to a method of imaging neuronal vesicular monoamine transporters. One of the key prerequisites for an in vivo imaging agent of the brain is the ability to cross the intact blood-brain barrier after a bolus iv injection. Compounds of the present invention have been shown by the data presented herein to possess this property.

In another aspect, the methods of imaging are directed to imaging pancreatic vesicular monoamine transporters. The compounds of the present invention have been shown by the data presented herein to possess affinity for pancreatic VMAT-2 transporters. This method is therefore useful for imaging beta cells of the pancreas, and also quantitatively determining the location, status, or any changes in, the beta cells. Beta cell densities in areas of the pancreas reflect "Beta Cell Mass" ("BCM"). Thus, the present method is useful for imaging beta cell densities and then determining BCM. Loss of BCM is likely to play an important role in the pathogenesis of T1D and T2D and presents an attractive target for therapeutic intervention. In addition, the ability to quantitate BCM in living patients will permit more efficient clinical evaluation of therapeutic strategies currently in development, including islet cell transplantation, islet cell protective therapies and islet cell regenerative therapies. BCM imaging may be useful for selecting patients for particular courses of therapy. For example, sulphonylureas act directly on islet beta cells to stimulate insulin secretion, a function which requires adequate remaining BCM in order to be effective.

The term "alkyl" as employed herein by itself or as part of another group refers to both straight and branched chain radicals of up to 8 carbons, preferably 6 carbons, more preferably 4 carbons, such as methyl, ethyl, propyl, isobutyl, butyl, t-butyl, and isobutyl.

The term "alkoxy" is used herein to mean a straight or branched chain alkyl radical, as defined above, unless the chain length is limited thereto, bonded to an oxygen atom, including, but not limited to, methoxy, ethoxy, n-propoxy, isopropoxy, and the like. Preferably the alkoxy chain is 1 to 6 carbon atoms in length, more preferably 1-4 carbon atoms in length.

The term "monoalkylamine" as employed herein by itself or as part of another group refers to an amino group which is substituted with one alkyl group as defined above.

The term "dialkylamine" as employed herein by itself or as part of another group refers to an amino group which is substituted with two alkyl groups as defined above.

The term "halo" or "halogen" employed herein by itself or as part of another group refers to chlorine, bromine, fluorine or iodine. As will be clear from the present disclosure, the term halo or halogen encompasses radioisotopes of the above listed halogens, i.e. radiohalogens.

The term "aryl" as employed herein by itself or as part of another group refers to monocyclic or bicyclic aromatic groups containing from 6 to 12 carbons in the ring portion, preferably 6-10 carbons in the ring portion, such as phenyl, naphthyl or tetrahydronaphthyl.

Racemic 9-fluoroethyl (FE) and 9-fluoropropyl (FP)-9-desmethyl-DTBZ and the corresponding hydroxyl derivatives were successfully prepared. No-carrier-added [18F]-DTBZ derivatives were synthesized by a [18F] fluoride displacement of the corresponding mesylates with good yields (30-40%) and high specific activity (S.A.=1,500-2,000 Ci/mmole). FE-DTBZ, 6a, and FP-DTBZ, 6b, displayed excellent binding affinities ($K_i$=0.76 and 0.56 nM, respectively) for VMAT2 binding sites in rat striatal homogenates. Consistently, [18F]6a and 6b exhibited $K_d$ values of 0.52 and 0.48 nM, respectively (based on S.A.=2000 Ci/mmole) for VMAT2 binding sites using mouse striatal homogenates. Both agents showed comparable binding densities to that obtained with [3H](±)tetrabenazine (TBZ). Results of in vitro autoradiography with [18F]6b showed a distinct binding in caudate putamen region consistent to the localization of VMAT2 in the mouse brain, which was blocked by non-radioactive TBZ efficiently. Biodistribution studies in mice after an iv injection of the tracer exhibited excellent brain uptakes (4.66 and 7.08% ID/g at 2 min for [18F]6a and [18F]6b, respectively). It was determined that [18F]6b displayed a faster brain washout than [18F]6a. As a result, [18F]6b yielded a better target (striatum, ST) to background (cerebellum, CB) ratio (ST/CB=3.0 and 1.9 for 6b and 6a, respectively). The blocking study with the non-radioactive DTBZ confirmed the in vivo competition and specificity of [18F]6b binding for VMAT2 sites.

The compounds of this invention can be prepared by reactions described in Schemes 1-4. The syntheses of cold and radiolabeled fluoroethyl and fluoropropyl derivatives of racemic (±)DTBZ, 2, are shown in Schemes 1, 2 and 3. Racemic FP-(±)-DTBZ yielded a HPLC profile with four distinct peaks. Retention times were 12.5 (peak 1), 18.3 (peak 2), 21.6 (peak 3) and 30.4 (peak 4), (FIG. 1). Optical resolution was performed using a HPLC system equipped with a chiral column-AD Chiracel.

Racemic tetrabenazine, (±)TBZ, 1, was reduced to dihydrotetrabenazine (±)DTBZ, 2, with sodium borohydride in ethanol. The methoxy group at the C-9 position of the tetrabenazine ring core was selectively demethylated (Kilbourn M R, Lee L C, Heeg M J, Jewett D M., Chirality, 1997:9:59-62) by heating DTBZ with sodium N-methyl anilide in HMPA and xylene at 65° C. to yield 9-O-desmethyl-DTBZ, 3 (Scheme 1). The latter compound served as the starting point for the synthesis of fluoroalkyl derivatives. First the "cold" fluoroethyl and fluoropropyl derivatives of (±)DTBZ were prepared. The 9-O-desmethyl-DTBZ, 3, was alkylated by 1-bromo-1-fluoro ethane or 3-fluoropropyl-p-toluenesulfonate with cesium carbonate at 110° C. in DMF to yield of fluoroethyl-DTBZ, 6a, and fluoropropyl-DTBZ, 6b, respectively (Scheme 2). A completely different approach for the synthesis of 18F radio labeled fluoroethyl and fluoropropyl DTBZ derivatives was adopted. The phenol in the compound 3 was alkylated with 2-bromo ethanol or 3-bromo-propanol to give 2-hydroxy ethyl, 4a or 3-hydroxy propyl, 4b, 9-desmethyl-DTBZ derivatives. These hydroxy compounds were mesylated with MsCl in methylene chloride at 0° C. to yield 5a and 5b. In the mesylation reaction only one equivalent of MsCl was used to avoid the mesylation of the hindered secondary hydroxy group at the C-2 position. These mesylates were then used as a precursor for the radiosynthesis of 18F labeled DTBZ derivatives.

To make the desired 18F labeled DTBZ derivatives, [18F]6a and 6b, the mesylates 5a and 5b were employed as the precursors (Scheme 3). Each of the mesylates, 5a or 5b, was mixed with [18F]fluoride/potassium carbonate and Kryptofix® 222 in DMSO and heated at 110° C. for 5-7 min. The crude product was purified by HPLC (radiochemical purity >99%, radiochemical yield 30-40%, decay corrected). The preparation of each 18F labeled compound, [18F]6a and 6b, took about 50-55 min and the specific activity was estimated to be 1,500-2,000 Ci/mmol at the end of synthesis.

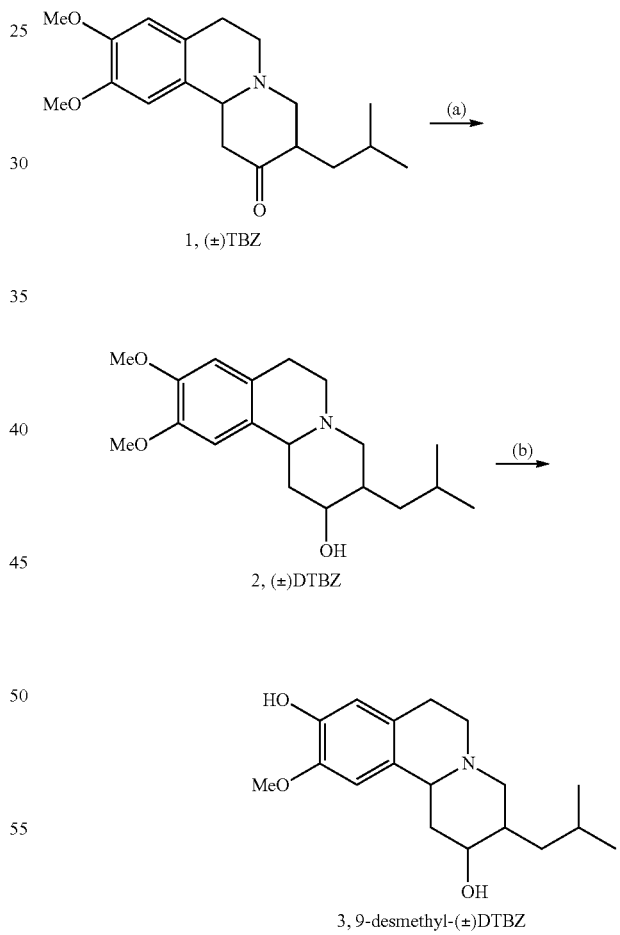

SCHEME 1

1, (±)TBZ 2, (±)DTBZ 3, 9-desmethyl-(±)DTBZ (a). NaBH₄, EtOH, RT, 1 hr, 100% (b). HMPA, N-methylaniline, xylene, NaH, 65° C., 48 hrs, 36%

SCHEME 2

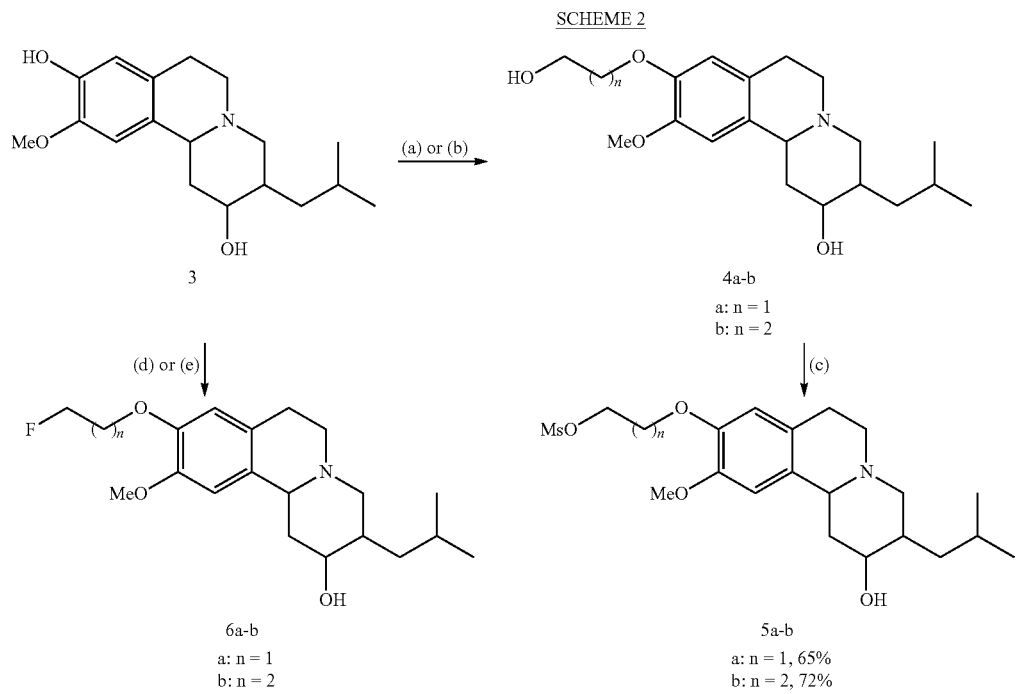

(a). HOCH₂CH₂Br (1.3 eq.), Cs₂CO₃ (1.5 eq.), DMF, 110° C., 16 hr, 60%; (b). HOCH₂CH₂CH₂Br (1.3 eq.), Cs₂CO₃ (1.5 eq.), DMF, 110° C., 16 hr, 70%; (c). MsCl (1.0 eq.), Et₃N (1.5 eq.), DCM, 0° C. to RT, 5 hr; (d). FCH₂CH₂Br (1.4 eq.), Cs₂CO₃ (1.4 eq.), DMF, 110° C., 15 hr, 60% or FCH₂CH₂Br (2 eq.), Cs₂CO₂ (2 eq.), NaI (2 eq.), DMF, 200° C., microwave 10 minutes, 50%; (e). FCH₂CH₂CH₂OTs (1.4 eq), Cs₂CO₃ (1.5 eq.), DMF, 110° C., 16 hr, 45%

SCHEME 4

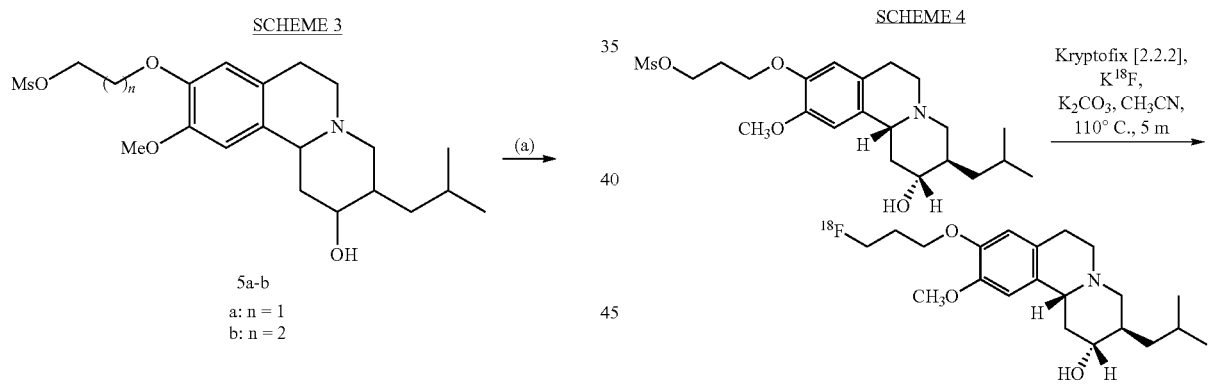

SCHEME 3

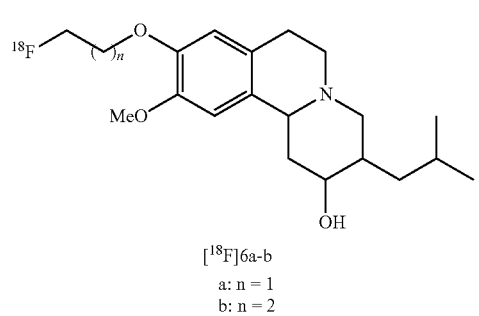

(a). K₂CO₃, Kryptofix [2.2.2], ¹⁸F anion, 110° C., 7 min

As shown in the following scheme, fluoropropyl (±)DTBZ can be synthesized by converting the hydroxyl compound into the corresponding tosylate or mesylate. Either of these intermediates is appropriate for further use towards the radiosynthesis. Separation via a Chiracel AD column yielded enantiomerically purified (+,+)₄b. Tosylation of (+,+)4b proceeded at about 35% yield. For the radiosyntheis of [¹⁸F](+,+) 6b, [¹⁸F]fluoride was eluted through a QMA anion-exchange cartridge and mixed with Kryptofix and potassium carbonate in acetonitrile:water. After azeotropic drying, 1 mg of (+,+)₅b dissolved in a 3:2 mixture of dimethylformamide and acetonitrile was added to the dried activities. The reaction was heated to 110° C. for 7 min., cooled to room temperature and purified using a solid phase cartridge (Waters Oasis). HPLC was utilized to yield [¹⁸F](+,+)6b in about 40% radiochemical yield with about 99% radiochemical purity. The specific activity of [¹⁸F](+,+)6b was from about 1500 to about 2000 Ci/mmol.

SCHEME 5
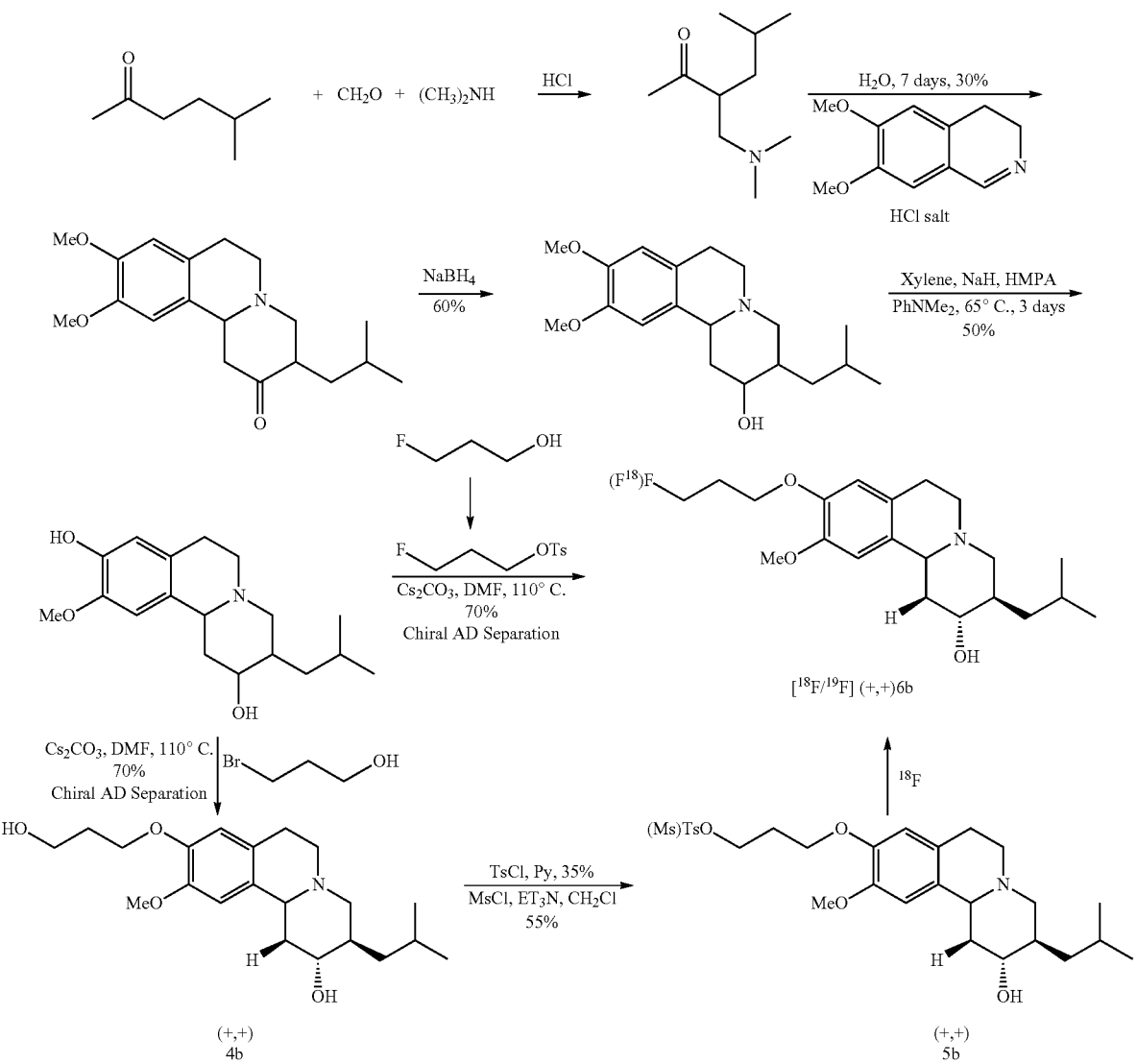
Compounds of the invention are synthesized using synthetic routes depicted in Schemes 6-9.
SCHEME 6
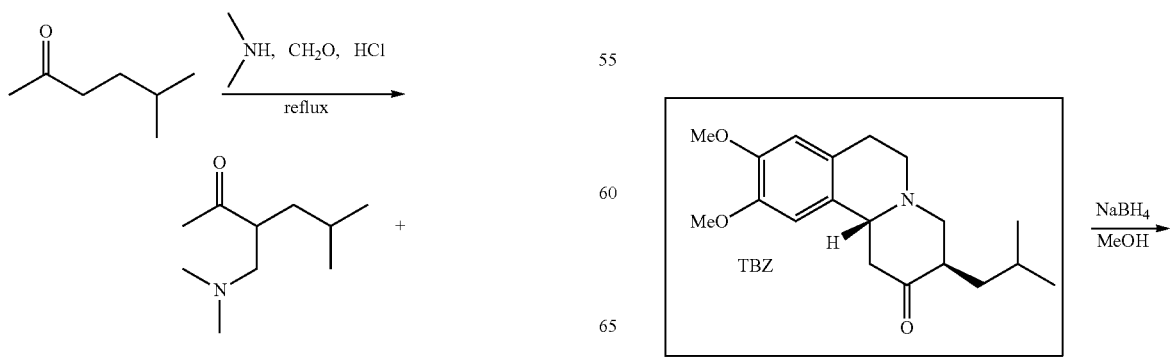

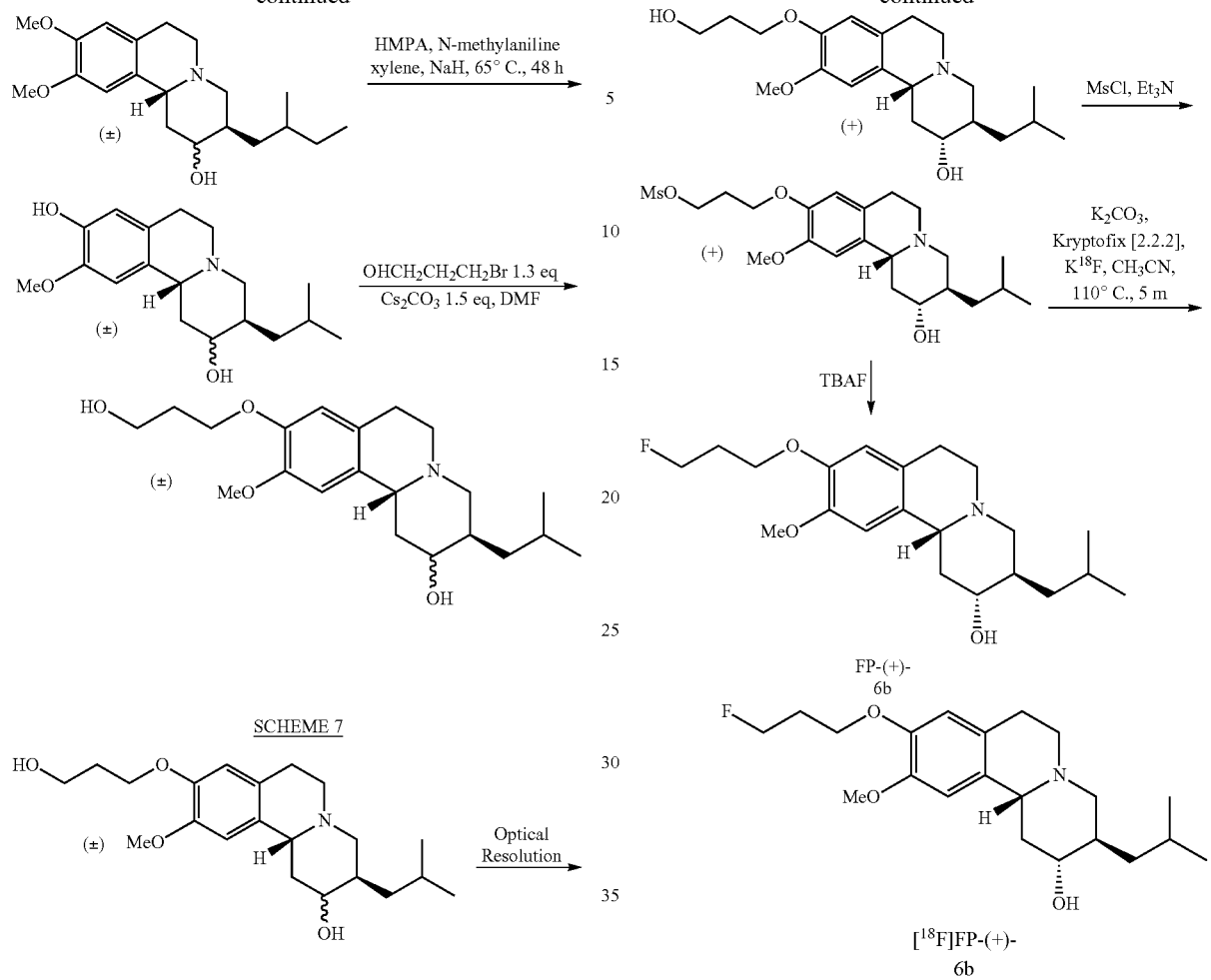
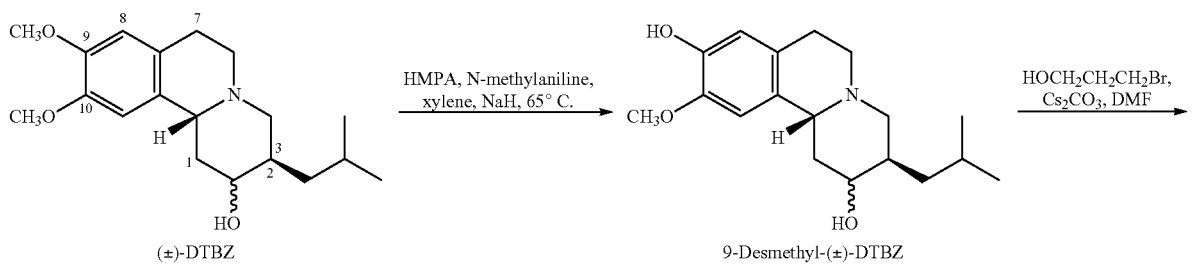
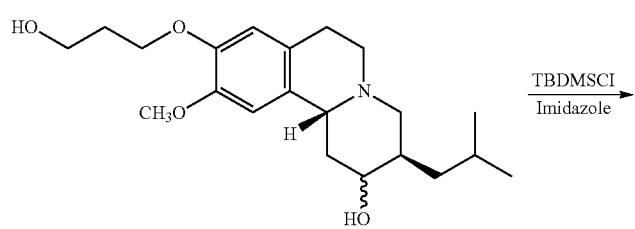

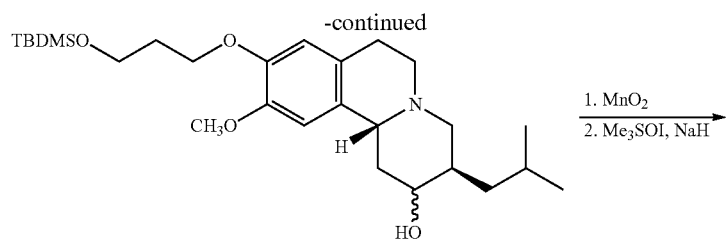
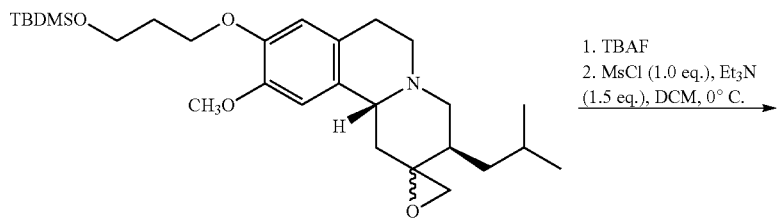
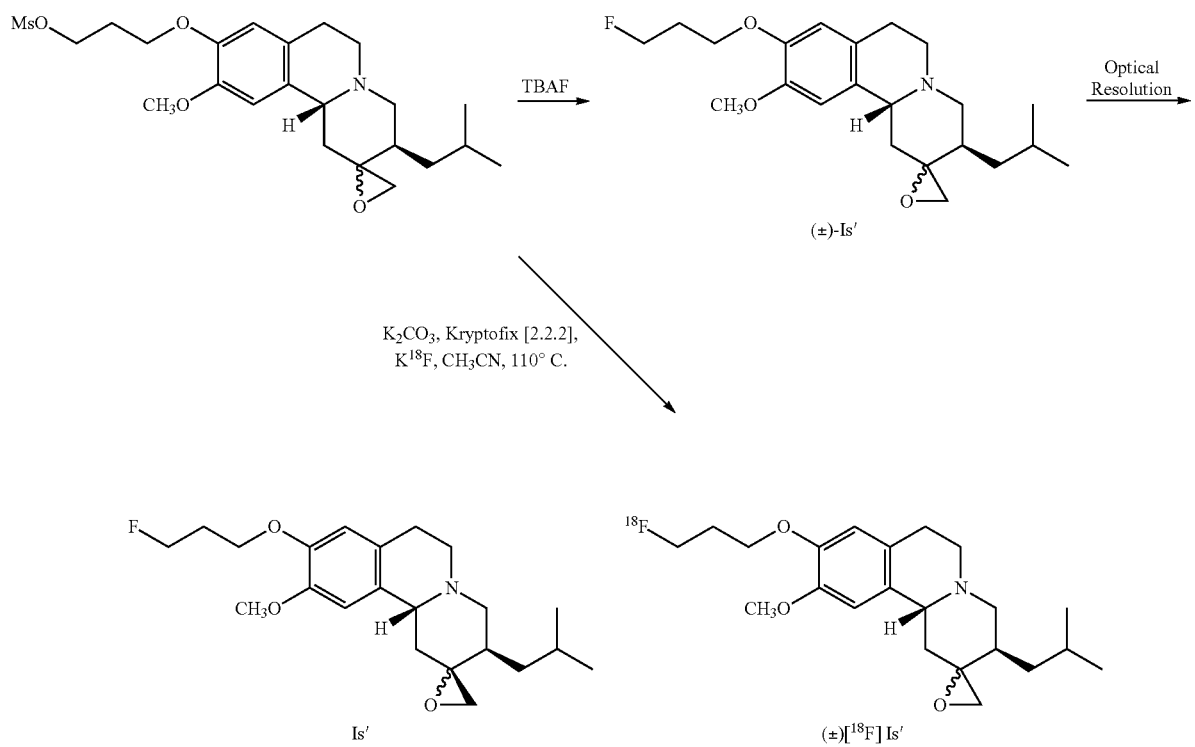
SCHEME 9
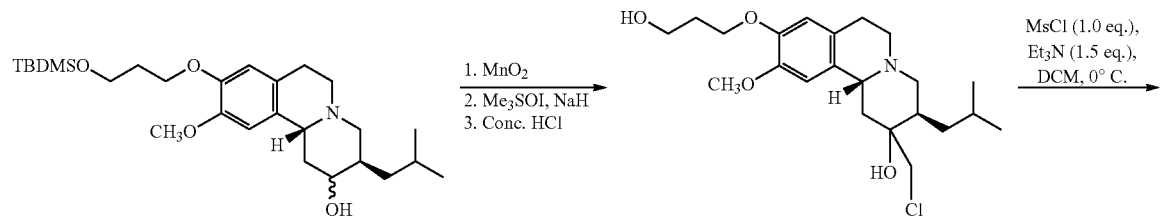

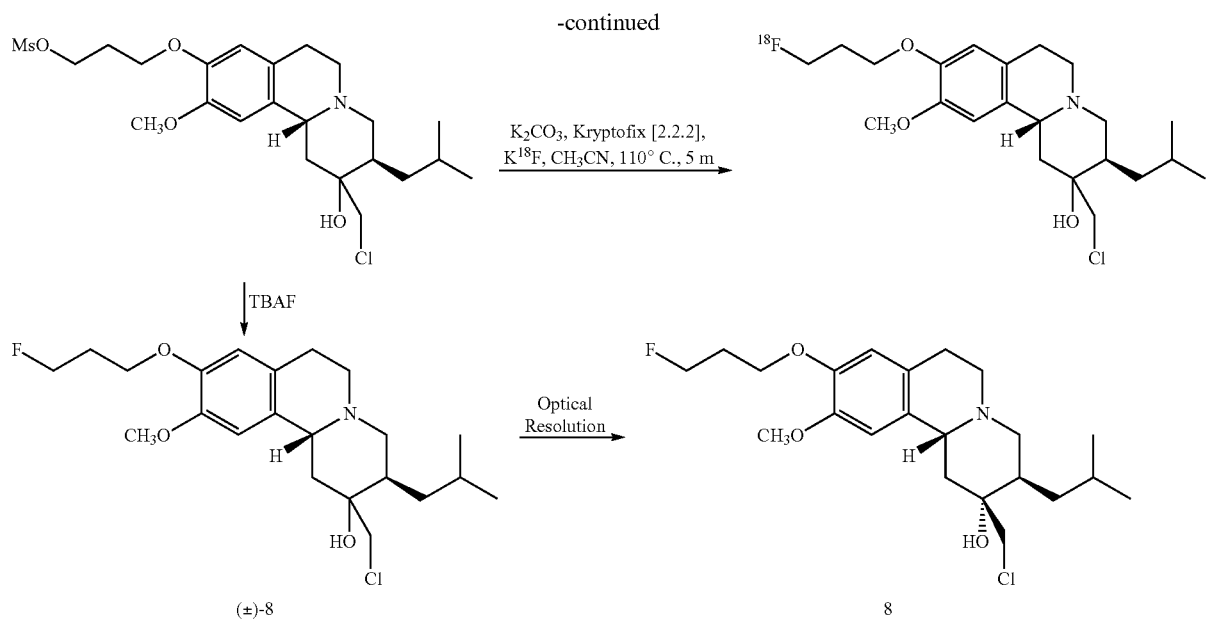

When the compounds of this invention are to be used as imaging agents, they must be labeled with suitable radioactive isotopes. Preferably, the isotope is a radiohalogen such as $^{123}$I, $^{125}$I, $^{131}$I, $^{18}$F, $^{76}$Br or $^{77}$Br. Most preferably, the halogen is a radiofluoride, such as $^{18}$F. Although $^{125}$I-isotopes are useful for laboratory testing, they will generally not be useful for actual diagnostic purposes because of the relatively long half-life (60 days) and low gamma-emission (30-65 Kev) of $^{125}$I. The isotope $^{123}$I has a half life of thirteen hours and gamma energy of 159 KeV, and it is therefore expected that labeling of ligands to be used for diagnostic purposes would be with this isotope. Other isotopes which may be used include $^{131}$I. Suitable bromine isotopes include $^{77}$Br and $^{76}$Br. The radioactive diagnostic agent should have sufficient radioactivity and radioactivity concentration which can assure reliable diagnosis. Determining sufficient radioactivity for the isotopes disclosed herein is well within the purview of those skilled in the art.

The radiolabeled compounds of this invention lend themselves easily to formation from materials which could be provided to users in kits. Kits for forming the imaging agents can contain, for example, a vial containing a physiologically suitable solution of an intermediate of Formulae I or II (including those of Formulae I' and II') in a suitable concentration and at a suitable pH. The user would add to the vial an appropriate quantity of the radioisotope, e.g., Na$^{123}$I, and an oxidant, such as hydrogen peroxide. The resulting labeled ligand may then be administered intravenously to a patient, and receptors in the brain imaged by means of measuring the gamma ray or photo emissions therefrom.

When desired, the radioactive diagnostic agent may contain any additive such as pH controlling agents (e.g., acids, bases, buffers), stabilizers (e.g., ascorbic acid) or isotonizing agents (e.g., sodium chloride).

The term "pharmaceutically acceptable salt" as used herein refers to those carboxylate salts or acid addition salts of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use, as well as the zwitterionic forms, where possible, of the compounds of the invention. The term "salts" refers to the relatively nontoxic, inorganic and organic acid addition salts of compounds of the present invention. Also included are those salts derived from non-toxic organic acids such as aliphatic mono and dicarboxylic acids, for example acetic acid, phenyl-substituted alkanoic acids, hydroxy alkanoic and alkanedioic acids, aromatic acids, and aliphatic and aromatic sulfonic acids. These salts can be prepared in situ during the final isolation and purification of the compounds or by separately reacting the purified compound in its free base form with a suitable organic or inorganic acid and isolating the salt thus formed. Further representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactiobionate and laurylsulphonate salts, propionate, pivalate, cyclamate, isethionate, and the like. These may include cations based on the alkali and alkaline earth metals, such as sodium, lithium, potassium, calcium, magnesium, and the like, as well as, nontoxic ammonium, quaternary ammonium and amine cations including, but not limited to ammonium, tetramethylammonium, tetraethylammonium, methylamine, dimethylamine, trimethylamine, triethylamine, ethylamine, and the like. (See, for example, Berge S. M., et al., *Pharmaceutical Salts, J. Pharm. Sci.* 66:1-19 (1977) which is incorporated herein by reference.)

In the first step of the present method of imaging, a labeled compound of Formulae I or II (including those of Formulae I' and II') is introduced into a tissue or a patient in a detectable quantity. The compound is typically part of a pharmaceutical composition and is administered to the tissue or the patient by methods well known to those skilled in the art. For example, the compound can be administered either orally, rectally, parenterally (intravenous, by intramuscularly or subcutaneously), intracisternally, intravaginally, intraperitoneally, intravesically, locally (powders, ointments or drops), or as a buccal or nasal spray. The administration of the labeled compound to a patient can be by a general or local administration route. For example, the labeled compound may be administered to the patient such that it is delivered throughout the body. Alternatively, the labeled compound can be administered to a specific organ or tissue of interest.

After sufficient time has passed for the compound to become associated with vesicular monoamine transporters, the labeled compound is detected noninvasively inside the patient. In another embodiment of the invention, a labeled compound of Formulae I or II (including those of Formulae I' and II') is introduced into a patient, sufficient time is allowed for the compound to become associated with vesicular monoamine transporters, and then a sample of tissue from the patient is removed and the labeled compound in the tissue is detected apart from the patient. In a third embodiment of the invention, a tissue sample is removed from a patient and a labeled compound of Formulae I or II (including those of Formulae I' and II') is introduced into the tissue sample. After a sufficient amount of time for the compound to become bound to vesicular monoamine transporters, the compound is detected. Preferably, the vesicular monoamine transporters are neuronal or pancreatic. If the radiohalogen present in the labeled compound is a positron emitter, such as $^{18}F$, then the method further provides for measuring the distribution of the composition within the mammal by positron emission tomography. If the radiohalogen present in the labeled compound is a single photon emitter, such as $^{123}I$, then the method further provides for measuring the distribution of the composition within the mammal by single photon emission tomography.

Those skilled in the art are familiar with the various ways to detect labeled compounds. For example, magnetic resonance imaging (MRI), positron emission tomography (PET), or single photon emission computed tomography (SPECT) can be used to detect radiolabeled compounds. The label that is introduced into the compound will depend on the detection method desired. For example, if PET is selected as a detection method, the compound must possess a positron-emitting atom, such as $^{11}C$ or $^{18}F$.

Those skilled in the art are also familiar with determining the amount of time sufficient for a compound to become associated with vesicular monoamine transporters. The amount of time necessary can easily be determined by introducing a detectable amount of a labeled compound of Formula I or II (including those of Formulae I' and II') into a patient and then detecting the labeled compound at various times after administration.

The term "patient" means humans and other animals. The term "tissue" means a part of a patient's body. Examples of tissues include the brain, heart, liver, blood vessels, and arteries. A detectable quantity is a quantity of labeled compound necessary to be detected by the detection method chosen. The amount of a labeled compound to be introduced into a patient in order to provide for detection can readily be determined by those skilled in the art. For example, increasing amounts of the labeled compound can be given to a patient until the compound is detected by the detection method of choice. A label is introduced into the compounds to provide for detection of the compounds.

The term "associated" means a chemical interaction between the labeled compound and one or more vesicular monoamine transporters. Examples of associations include covalent bonds, ionic bonds, hydrophilic-hydrophilic interactions, hydrophobic-hydrophobic interactions, and complexes.

The binding affinities of nonradioactive 6a and 6b for VMAT2 were determined by using [$^3H$](±)TBZ as the radioligand in rat striatal tissue homogenates (Table 1). Both 6a and 6b displayed excellent binding affinities with $K_i$ values of 0.76 and 0.56 nM, respectively for VMAT2. The corresponding hydroxyethyl- and hydroxypropyl-derivatives 4a and 4b showed much lower binding affinities ($K_i$=48.5 and 75.8 nM, respectively). In addition, we estimated the dissociation constants ($K_d$ values) for the radiofluorinated probes, [$^{18}F$]6a and [$^{18}F$]6b, using mouse striatal homogenates. Consistently, the $K_d$ values estimated based on S.A=2,000 Ci/mmole were found to be 0.52±0.04 and 0.48±0.01 nM for [$^{18}F$]6a and [$^{18}F$]6b, respectively (data not shown). The $K_d$ values are consistent with the $K_i$ values measured by competition experiments.

The lipophilicity of these series of TBZ derivatives was determined to be as follows: (partition coefficient=131 and 411, measured between 1-octanol and phosphate buffer for [$^{18}F$]6a and [$^{18}F$]6b, respectively). Both $^{18}F$ labeled probes penetrated readily through intact blood-brain barrier showing excellent brain uptakes in normal mice (4.66% and 7.08% dose/g for [$^{18}F$]6a and [$^{18}F$]6b, respectively at 2 min post-intravenous injection) (Table 2). [$^{18}F$]6b showed a faster brain washout (13% remaining at 30 min p.i.) as compared to [$^{18}F$]6a (>50% remaining at 30 min, p.i.). Liver and kidney are two major organs for the excretion of both $^{18}F$ labeled derivatives. The higher bone uptake observed for [$^{1F}$]6b as compared to [$^{18}F$]6a (9.62% vs 3.88% dose/g, respectively) indicated that likely there was a faster in vivo defluorination for [$^{18}F$]6b. Both fluorinated ligands exhibited significant localization in monoamine enriched structures, with striatum (ST) the highest (Table 2). Using cerebellum (CB) as the background region (nontarget region containing a minimal amount of VMAT2), the ST/CB ratio reached the peak of 3.0 at 30 min p.i. for [$^{18}F$]6b. This value is comparable to the values reported for [$^{11}C$]DTBZ (Kilbourn M, Sherman P. In vivo binding of (+)-[alpha]-[$^3H$]dihydrotetrabenazine to the vesicular monoamine transporter of rat brain: bolus vs. equilibrium studies, *Eur. J. Pharmacol.*, 1997:331:161-68). A steady ratio (ST/CB) was observed from 15 min to 60 min for [$^{18}F$]6b. Unexpectedly, the ST/CB ratios for [$^{18}F$]6a were found to be lower (1.91, 1.71 and 1.71 for 15, 30 and 60 min, p.i., respectively). The favorable in vivo kinetic properties associated with the fluoropropyl derivative, [$^{18}F$]6b (higher brain uptake and fast background washout), appeared to contribute to the better target (ST) to nontarget (CB) ratios. These ratios obtained were for the racemic mixtures (theoretically containing 50% of the active isomer. (Kilbourn M, Lee L, Borght T V, Jewett D, Frey K. Binding of [alpha]-dihydrotetrabenazine to the vesicular monoamine transporter is stereospecific, *Eur. J. Pharmacol.*, 1995:278:249-52).

Figure 2:
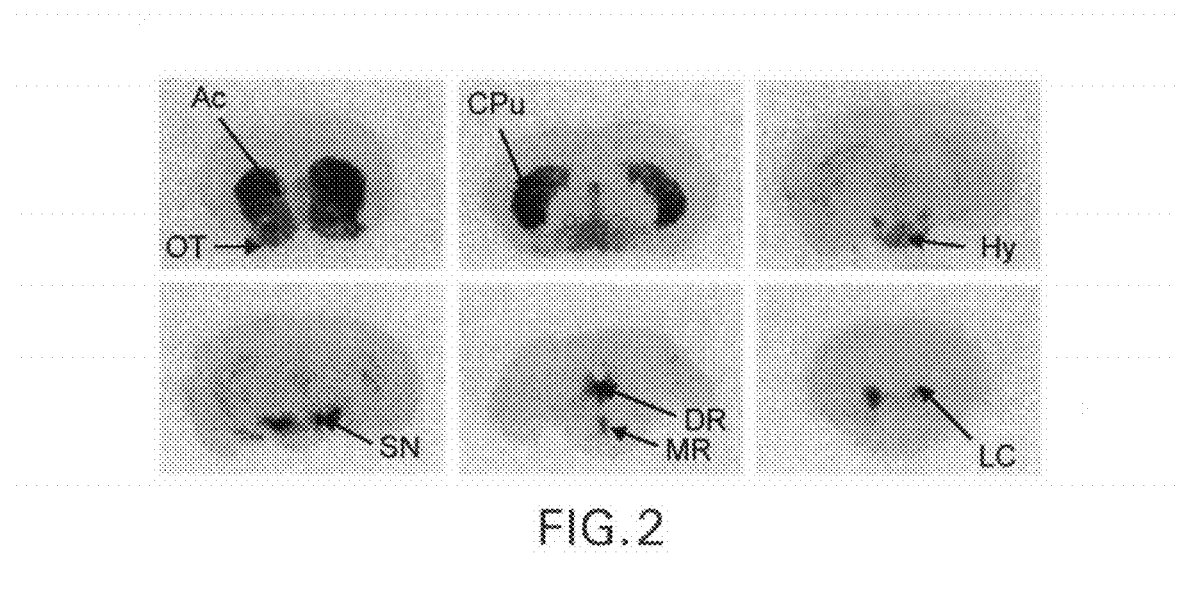
FIG. 2 depicts an ex vivo autoradiography of a normal mouse brain revealing the anatomical localization of VMAT sites labeled by [$^{18}$F]FP-(+)-DTBZ. 500 µCi [$^{18}$F]FP-(+)-DTBZ was injected into a normal ICR mouse and the mouse was sacrificed at 30 minutes post-injection. High density labeled sites reflect the regional distribution of monoaminergic neurons in the brain: CPu, caudate putamen; OT, olfactory tubercle; Ac, nucleus accumbens; Hy, hypothalamic nucleus; SN, substantia nigra; DR, dorsal raphe; MR, median raphe; LC, locus coeruleus.

The binding specificity for VMAT2 of fluorinated DTBZ ligands, 6a and 6b, was further confirmed by a blocking experiment. As shown in Table 3, co-injection of (±)DTBZ (3 mg/kg), a well characterized specific VMAT2 ligand, with [$^{18}F$]6b completely abolished the selective localization resulting in the ratio of ST/CB close to unity (3.40 vs 0.98, see Table 3). In contrast, co-injection of [$^{18}F$]6b with the non-VMAT2 ligand, i.e. raclopride (1.2 mg/kg), a dopamine D2/D3 receptor antagonist, did not affect the target (ST) to non-target (CB) ratio (3.40 vs 3.93, respectively). Furthermore, the in vitro autoradiography clearly indicated the similarity of regional localization between [$^3H$]TBZ and [$^{18}F$]6b. A region rich in VMAT2 binding site, i.e. basal ganglia, in the mouse brain, showed the highest binding of [$^{18}F$]6b (FIG. 2). Regions corresponding to caudate putamen, olfactory tubercle and nucleus accumbens can be clearly visualized. These distinct regional labeling were completely eliminated in the presence of 1 µM (±)TBZ (data not shown) indicating that TBZ and the radiofluorinated ligand, [$^{18}F$]6b are competing for the same VMAT2 sites in the brain.

The following examples are illustrative, but not limiting, of the method and compositions of the present invention. Other suitable modifications and adaptations of the variety of conditions and parameters normally encountered and obvious to those skilled in the art are within the spirit and scope of the invention.

All reagents used in synthesis were commercial products and were used without further purification unless otherwise indicated. $^1$H NMR spectra were obtained on a Bruker DPX spectrometer (200 MHz) in CDCl$_3$. Chemical shifts are reported as δ values (parts per million) relative to internal TMS. Coupling constants are reported in hertz. The multiplicity is defined by s (singlet), d (doublet), t (triplet), br (broad), m (multiplet).

EXAMPLE 1

Synthesis (±)-2-hydroxy-3-isobutyl-9-(2-hydroxyethoxy)-10-methoxy-1,2,3,4,6,7-hexahydro-11bH-benzo[a]quinolizine (4a)

To (±)-9-O-Desmethyldihydrotetrabenazine (3) (35 mg, 0.11 mmol), prepared as reported previously [15], in dry DMF (1.5 ml), Cs$_2$CO$_3$ (49 mg, 10.15 mmol) was added and the mixture stirred for 30 minutes at room temperature. A DMF (0.5 ml) solution of 2-bromo-ethanol (17.8 mg, 0.14 mmol) was added to the resultant orange solution. The mixture was stirred at 110° C. for 18 hours during which solution turned dark red. The mixture was then quenched with H$_2$O (10 ml) and the aqueous phase extracted with EtOAc (3×25 ml). The combined organic extracts were dried over MgSO$_4$, evaporated and purified by the flash column chromatography [R$_f$=0.18, (MeOH/dichloromethane 5:95, v/v)] to afford 24 mg of the resultant alcohol (4a) as yellow oil in 60% yield; 1H-NMR (CDCl$_3$) δ 0.90 (d, J=4.3 Hz, 3H), 0.93 (d, J=4.2 Hz, 3H), 1.06 (m, 1H), 1.55-1.83 (m, 5H), 2.0 (t, J=11.2 Hz, 1H), 2.24-2.67 (m, 4H), 2.97-3.19 (m, 4H), 3.35-3.43 (m, 1H), 3.80 (s, 3H, major diastereomer), 3.82 (s, 3H, minor diastereomer), 3.89 (t, J=4.5 Hz, 2H), 4.08 (t, J=4.6 Hz, 2H), 6.59 (s, 1H, minor diastereomer), 6.63 (1H, major diastereomer), 6.67 (s, 1H, major diastereomer), 6.73 (s, 1H, minor diastereomer); HRMS calc. For C$_{20}$H$_{31}$NO$_4$ [M+] 349.2253, found 349.2243.

(±)-2-hydroxy-3-isobutyl-9-(2-methanesulfonyloxy-ethoxy)-10-methoxy-1,2,3,4,6,7-hexahydro-1bH-benzo[a]quinolizine (5a)

To a solution containing hydroxy quinolizine (4a) (38 mg, 0.11 mmol) and Et$_3$N (22.3 mg, 0.22 mmol) in dry dichloromethane (1.7 ml), MsCl (12.5 mg, 0.11 mmol) in dichloromethane (0.5 ml) was added dropwise at 0° C. and the mixture stirred for 4 hours. The reaction mixture was then quenched with H$_2$O (10 ml) and the aqueous phase extracted with dichloromethane (3×25 ml). The combined organic extracts were dried over MgSO$_4$, evaporated and purified by the flash column chromatography [R$_f$=0.45, (MeOH/dichloromethane 5:95, v/v)] to afford 26 mg of the resultant mesylate (5a) as white fluffy solid in 56% yield along with 11.4 mg of starting material; $^1$H-NMR (CDCl$_3$) δ 0.92 (d, J=5.7 Hz, 3H), 0.94 (d, J=4.6 Hz, 3H), 1.0 (m, 1H), 1.49-1.80 (m, 5H), 2.01 (t, J=11.2 Hz, 1H), 2.48-2.68 (m, 3H), 3.02-3.1 (m, 4H), 3.13 (s, 3H), 3.32-3.47 (m, 1H), 3.8 (s, 3H), 4.23 (t, J=4.6 Hz, 2H), 4.57 (t, J=4.3 Hz, 2H), 6.57 (s, 1H, major and minor diastereomers), 6.67 (s, 1H, major diastereomer), 6.72 (s, 1H, minor diastereomer); HRMS calc. For C$_{21}$H$_{33}$NO$_6$S [M+] 427.2029, found 427.2004.

(±)-2-hydroxy-3-isobutyl-9-(2-fluoroethoxy)-10-methoxy-1,2,3,4,6,7-hexahydro-11bH-benzo[a]quinolizine (6a)

(±)-9-O-Desmethyldihydrotetrabenazine (3) (30 mg, 0.1 mmol) was dissolved in dry DMF (1.0 ml) in a 2 ml microwave tube under argon, Cs$_2$CO$_3$ (64 mg, 0.19 mmol) was added and the mixture stirred for 20 minutes at room temperature during which yellow solution turned orange. NaI (30 mg, 0.19 mmol) and a DMF (0.5 ml) solution of 1-bromo-2-fluoroethane (25.4 mg, 0.19 mmol) were then added and the mixture heated at 200° C. in microwave for 10 minutes. The brown solution was then quenched with H2O (10 ml) and the aqueous phase extracted with EtOAc (3×25 ml). The combined organic extracts were dried over MgSO$_4$, evaporated and purified by the flash column chromatography [R$_f$=0.25, MeOH/dichloromethane 5:95, v/v)] to afford 17.3 mg of the fluoride (6a) as yellow solid in 50% yield; $^1$H-NMR (CDCl$_3$) δ 0.90 (d, J=5.5 Hz, 3H), 0.93 (d, J=4.9 Hz, 3H), 1.04 (m, 1H), 1.48-1.82 (m, 5H), 1.99 (t, J=11.4 Hz, 1H), 2.4-2.7 (m, 3H), 3.0-3.15 (m, 4H), 3.3-3.48 (m, 1H), 3.82 (s, 3H), 4.22 (dt, J=27.5, 4.3 Hz, 2H), 4.74 (dt, J=47.3, 4.1 Hz, 2H), 6.53 (s, 1H, minor diastereomer), 6.56 (s, 1H, major diastereomer), 6.62 (s, 1H, major diastereomer), 6.68 (s, 1H, minor diastereomer); HRMS calc. For C$_{20}$H$_{30}$FNO$_3$ [M+] 351.2210, found 351.2226.

(±)-2-hydroxy-3-isobutyl-9-(3-hydroxypropoxy)-10-methoxy-1,2,3,4,6,7-hexahydro-1 bH-benzo[a]quinolizine (4b)

To a yellow solution of (±)-9-O-Desmethyldihydrotetrabenazine (3) (70 mg, 0.22 mmol) in dry DMF (2.5 ml), Cs$_2$CO$_3$ (97 mg, 0.3 mmol) was added and the mixture stirred for 30 minutes at room temperature. A DMF (0.5 ml) solution of 3-bromo-propanol (41.4 mg, 0.3 mmol) was then added to the resultant orange solution. The mixture was stirred at 110° C. for 18 hours during which solution turned dark red. The mixture was quenched with H$_2$O (10 ml) and the aqueous phase extracted with EtOAc (3×25 ml). The combined organic extracts were dried over MgSO$_4$, evaporated and purified by the flash column chromatography [R$_f$=0.18, MeOH/dichloromethane 5:95, v/v)] to afford 59 mg of the resultant alcohol (4b) as yellow oil in 71% yield; 1H-NMR (CDCl$_3$) δ 0.90 (d, J=4.4 Hz, 3H), 0.93 (d, J=4.4 Hz, 3H), 1.04 (m, 1H), 1.49-1.90 (m, 5H), 1.98-2.07 (m, 3), 2.46-2.66 (m, 4H), 3.0-3.19 (m, 4H), 3.30-3.48 (m, 1H), 3.80 (s, 3H), 3.85 (t, J=5.4 Hz, 2H), 4.14 (t, J=5.8 Hz, 2H), 6.57 (s, 1H, minor diastereomer), 6.60 (s, 1H, major diastereomer), 6.66 (s, 1H, major diastereomer), 6.72 (s, 1H, minor diastereomer); HRMS calc. For C$_{21}$H$_{33}$NO$_4$ [M+] 363.2410, found 363.2404.

(±)-2-hydroxy-3-isobutyl-9-(3-methanesulfonyloxypropoxy)-10-methoxy-1,2,3,4,6,7-hexahydro-11 bH-benzo[a]quinolizine (5b)

To hydroxy quinolizine (4b) (50 mg, 0.14 mmol) and Et3N (27.7 mg, 0.27 mmol) in dry dichloromethane (2.5 ml), a dichloromethane (0.5 ml) solution of MsCl (15.7 mg, 0.14 mmol) was added dropwise at 0° C. After stirring for 4 hours the reaction mixture was quenched with H$_2$O (10 ml) and the aqueous phase extracted with dichloromethane (3×25 ml).

The combined organic extracts were dried over MgSO$_4$, evaporated and purified by the flash column chromatography [R$_f$=0.45, MeOH/dichloromethane 5:95, v/v)] to afford 24 mg of the mesylate (5b) as white fluffy solid in 40% yield along with 15 mg of recovered starting material; $^1$H-NMR (CDCl$_3$) δ 0.91 (d, J=4.1 Hz, 3H), 0.93 (d, J=4.6 Hz, 3H), 1.06 (m, 1H), 1.54-1.72 (m, 5H), 2.0 (t, J=11.4 Hz, 1H), 2.2-2.26 (m, 2H), 2.54-2.70 (m, 3H), 2.98 (s, 3H), 2.99-3.09 (m, 4H), 3.30-3.45 (m, 1H), 3.79 (s, minor diastereomer), 3.80 (s, 3H, major diastereomer), 4.09 (t, J=5.8 Hz, 2H), 4.45 (t, J=6.0 Hz, 2H), 6.60 (s, 1H, major and minor diastereomers), 6.67 (s, 1H, major diastereomer), 6.67 (s, 1H, minor diastereomer); HRMS calc. For C$_{22}$H$_{35}$NO$_6$S [M+] 441.2185, found 441.2172.

3-fluoropropyl-p-toluenesulfonate

To 3-fluoro-propan-1-ol (0.2 gm, 2.56 mmol) in dichloromethane (7 ml), DMAP (63 mg, 0.5 mmol) and pyridine (0.4 mg, 5.12 mmol) were added. Mixture cooled down to 0° C. then TsCl (0.73 gm, 3.84 mmol) was added and mixture stirred overnight. 1M HCl (10 ml) was added and the layers were separated. The aqueous phase was extracted in dichloromethane (3×40 ml). The combined organic extracts were dried over MgSO$_4$, evaporated and purified by flash column chromatography to give 0.447 gm of the tosylate in 70% yield; $^1$H-NMR (CDCl$_3$) δ 2.02 (dquint, J=25.8, 5.9 Hz, 2H), 2.45 (s, 3H), 4.16 7(t, J=6.14 Hz, 2H), 4.47 (dt, J=46.8, 5.6 Hz, 2H), 7.35 (d, J=7.9 Hz, 2H), 7.80 (d, J=8.2 Hz, 2H).

(±)-2-hydroxy-3-isobutyl-9-(3-fluoropropoxy)-10-methoxy-1,2,3,4,6,7-hexahydro-11bH-benzo[a]quinolizine (6b)

(±)-9-O-Desmethyldihydrotetrabenazine (3) (43 mg, 0.14 mmol) was dissolved in dry DMF (1.0 ml) under argon, Cs$_2$CO$_3$ (60 mg, 0.18 mmol) was added and the mixture stirred for 20 minutes at room temperature during which yellow solution turned orange. A DMF (0.5 ml) solution of 3-fluoropropyl-p-toluenesulfonate (8) (43 mg, 0.18 mmol) was added and the mixture heated at 110° C. for 18 hours. The dark red solution was then quenched with H$_2$O (10 ml) and the aqueous phase extracted with EtOAc (3×25 ml). The combined organic extracts were dried over MgSO$_4$, evaporated and purified by the flash column chromatography [R$_f$=0.25, MeOH/dichloromethane 5:95, v/v)] to afford 29.8 mg of the fluoride (6b) as solid in 45% yield; $^1$H-NMR (CDCl$_3$) δ 0.91 (d, J=4.7 Hz, 3H), 0.94 (d, J=4.5 Hz, 3H), 1.04 (m, 1H), 1.48-1.85 (m, 5H), 2.0 (t, J=11.4 Hz, 1H), 2.19 (dquint, J=26.2, 5.9 Hz, 2H), 2.37-2.74 (m, 3H), 2.90-3.22 (m, 4H), 3.25-3.40 (m, 1H), 3.74 (s, 3H), 4.11 (t, J=6.2 Hz, 2H), 4.64 (dt, J=47, 5.7 Hz, 2H), 6.58 (s, 1H, minor diastereomer), 6.61 (s, 1H, major diastereomer), 6.68 (s, 1H, major diastereomer), 6.73 (s, 1H, minor diastereomer); HRMS calc. For C$_{21}$H$_{32}$FNO$_3$ [M+] 365.2366, found 365.2350.

EXAMPLE 2

Radiosynthesis

[$^{18}$F]Fluoride was produced by cyclotron irradiation of [$^{18}$O]water, and isolated by passing the target water through a Sep-Pak Light QMA cartridge. The [$^{18}$F]fluoride ion was eluted from the QMA cartridge with 1 mL solution of acetonitrile (0.8 mL) and water (0.2 mL) containing Kryptofix (13 mg) and potassium carbonate (0.2 mg). The Water was azeotropically evaporated from this mixture using HPLC grade acetonitrile (3×0.5 mL) in an oil bath at 110° C. under a stream of nitrogen. After the final drying sequence, 1 mg of 5a or 5b dissolved in 0.5 mL of DMF: ACN (3:2) were added to the $^{18}$F residue. The content were briefly mixed using nitrogen and heated at 110° C. for 5 minutes. Then reaction mixture was diluted with water (6 mL). Solid phase purification was performed using a Waters (HLB-6 cc, part no 186000115, 200 mg) Oasis® cartridge previously rinsed with a solution of 5% ethanol in water (10 mL). After the radioactive sample had been applied, the cartridge was rinsed with additional 3×6 mL water to eliminate unreacted fluoride, and the radiolabeled product was eluted with acetonitrile (4 mL). When the evaporation of 2 mL of acetonitrile was completed then 3 mL of water was added and then it was purified by semi-preparative HPLC. The quality control of [$^{18}$F]6a and [$^{18}$F]6b showed the product eluting at 4.9 and 6.5 min, respectively and co-eluting with non-radioactive standard 6a and 6b in the analytical HPLC. The area of UV peak corresponding to the product was compared with a standard calibration curve and was used to determine specific activity of [$^{18}$F]6a or [$^{18}$F]6b. The specific activity of [$^{18}$F]6a and [$^{18}$F]6b was estimated around 2000 Ci/mmol. The complete synthesis required about 50-55 minutes; the radiochemical purity was >98% and radiochemical yield was 40±5 (decay corrected).

EXAMPLE 3

HPLC Purification

Two HPLC systems were used to confirm the purities of the compounds 4a, 4b, 6a and 6b. Greater than 95% purity was obtained for both of the fluoroethyl and fluoropropyl derivatives, 6a and 6b as well as for both of the hydroxy derivatives, 4a and 4b.

System A: Agilent 1100 series HPLC, column: Phenomenex, Luna 5□, C-18, 250×4.6 mm and solvent system was 1:2 (acetonitrile: 50 mM ammonium acetate solution, pH 4.5 adjusted by phosphoric acid) at a flow rate of 1 mL/min with UV at 280 nm. Retention time: 6a, 4.9 min; 6b, 6.1 min; 0.4a, 2.6 & 3.0 min; 4b, 2.6 & 3.2 min System B: Ranin HPLC, column: Hamilton PRP-1, 5□, 250×4.6 mm and solvent system was 7:3 (acetonitrile: 5 mM dimethylglutaric acid, pH 7.0) at a flow rate of 0.5 ml/min with UV at 280 nm. Retention time: 6a, 8.7 min; 6b, 10.2 min; 0.4a, 6.0 min; 4b, 6.4 min.

Semi-preparative HPLC condition: Agilent 1100 series HPLC, Column: Phenomenex, Luna 5 u, C-18, 250×10 mm and solvent system was 1:2 (acetonitrile: 50 mM ammonium acetate solution, pH 4.5 adjusted by phosphoric acid) at a flow rate of 3 mL/min. Analytical HPLC condition: Agilent 1100 series HPLC, Column: Phenomenex, Luna 5 u, C-18, 250× 4.6 mm and solvent system was 1:2 (acetonitrile: 50 mM ammonium acetate solution, pH 4.5 adjusted by phosphoric acid) at a flow rate of 1 mL/min with UV at 240 nm. HPLC retention time of [$^{18}$F]6a and [$^{18}$F]6b was 4.9 min and 6.5 min, respectively.

EXAMPLE 4

Homogenate Binding

The basal forebrain regions of rat and mouse brains were then dissected. The tissue homogenates were prepared in 50 mM Hepes, pH 7.5 and 0.3 M sucrose. The specific binding of $^3$H or $^{18}$F ligands were determined following the procedures described (Scherman D, Raisman R, Ploska A, Agid Y., [$^3$H] Dihydrotetrabenazine, a new in vitro monoaminergic probe for human brain, *J. Neurochem.*, 1988:50:1131-36). Total volume of reaction for the assay was 0.2 ml. In competition experiments, compounds at concentrations up to 10-5M were examined for their abilities to compete for the binding of [$^3$H](±)TBZ (1.0-1.5 nM). In saturation experiments, increasing concentrations of labeled ligand (0.01-0.5 mM) in 50 µl buffer were incubated with 100 µl of homogenates (100-250 µg). Incubation was carried out routinely at room temperature for 90 min. The samples were then filtered through glass fiber filters No. 25 (Schleicher and Schuell, Keene, N.H.) and the bound radioactivity was determined for $^{18}$F in a gamma counter (Packard 5000) with 70% efficiency. Filters containing bound $^3$H ligand were dissolved in 7 ml Ecolite(+) overnight and the radioactivity was counted next day in the scintillation counter (Beckman) with 65% counting efficiency. Protein determinations were performed with Lowry et al's method (Lowry O H, Rosebrough N J, Farr A L, Randall R J., Protein measurement with Folin phenol reagent, *J. Biol. Chem.*, 1951:193:265-75) using bovine serum albumin as a standard. Nonspecific binding was determined in the presence of 10 µM tetrabenazine. Both saturation and competition experiments were analyzed using the nonlinear least-square curve fitting program LIGAND. (Munson P J, Rodbard D., LIGAND: a versatile computerized approach for characterization of ligand-binding systems, *Anal. Biochem.*, 1980:107: 220-39.) The results are shown in Table 1.

TABLE 1

| Compound | Ki (nM ± SEM) |
|---|---|
| 1,TBZ | 1.3 ± 0.1 |
| 3,9-desmethyl-(±)DTBZ | 11.8 ± 1.7 |
| 6a | 0.76 ± 0.1 |
| 6b | 0.58 ± 0.03 |
| 4a | 75.8 ± 3.5 |
| 4b | 48.5 ± 8.8 |

Kd of 8.1 nM for [$^3$H](±)TBZ was used for the calculation based on the Ki value reported previously (Kilbourn M, Sherman P., In vivo binding of (+)-[alpha]-[$^3$H]dihydrotetrabenazine to the vesicular monoamine transporter of rat brain: bolus vs. equilibrium studies, *Eur. J. Pharmacol.*, 1997: 331: 161-68.)

EXAMPLE 5

Autoradiographic Studies

For in vitro autoradiographic studies, mice were anesthetized with isoflurane and sacrificed by cervical dislocation; the brains were removed immediately and frozen with powdered dry ice. Coronal sections of 20 µm thickness were cut on a cryostat microtome, thaw-mounted onto Fisher superfrost plus slides, and stored at −20° C. until use. Prior to each binding assay, sections were thawed, dried at room temperature, and pre-incubated for 20 min in ice-cold incubation buffer (10 mM Hepes, pH 7.5). The incubation was then carried out in coplin jars in buffer (10 mM Hepes, pH 7.5, 0.3 M sucrose and 0.1% bovine serum albumin) containing 4.6 nM [$^3$H](±)TBZ or 1.28 nM [$^{18}$F]6b for 90 min. After the incubation, the sections were rinsed in ice-cold Hepes buffer twice for 30 min each time. Tissue sections were then dipped in ice-cold distilled water 30 sec to remove buffer salts before drying in a stream of cold air. Adjacent sections were labeled similarly but in the presence of 10 µM tetrabenazine to define nonspecific binding. The dried tissue sections were then exposed to Kodak Biomax MR film for $^{18}$F tracer (overnight) in an autoradiographic cassette together with 20 µm thick $^{125}$I standards (Amersham, Arlington Heights, Ill.). Exposure for $^3$H ligand was done using Amersham Hyperfilm for 6 weeks.

EXAMPLE 6

Organ Distribution in Normal Mice

While under isoflurane anesthesia, 0.15 mL of a 0.1% bovine serum albumin solution containing [$^{18}$F]tracers (10-20 µCi) were injected directly into the tail vein of ICR mice (22-25 g, male) The mice (n=3 for each time point) were sacrificed by cervical dislocation at indicated time points post injection. The organs of interest were removed and weighed, and the radioactivity was counted with an automatic gamma counter. The percentage dose per organ was calculated by a comparison of the tissue counts to suitably diluted aliquots of the injected material. Total activities of blood were calculated under the assumption that they were 7% of the total body weight. The % dose/g of samples was calculated by comparing the sample counts with the count of the diluted initial dose. Different regions corresponding to striatum (ST), hippocampus (HP), cerebellum (CB), and cortex (CX) were dissected out from the brain.

Blocking studies were carried out by co-injection (iv) of the $^{18}$F tracer with (±)DTBZ (3 mg/kg) or raclopride (1.2 mg/kg) into the animals. Thirty minutes after the injection, the animals were sacrificed and the brain regions including ST, HP, CB and CX were dissected out and the % dose/g were calculated. The ratios of target (ST) vs nontarget (CB) were compared between control and blocked groups.

TABLE 2

Biodistribution of [$^{18}$F]6a and [$^{18}$F]6b in normal mice (iv injection)

| | 2 min | 15 min | 30 min | 1 hr | 2 hr |
|---|---|---|---|---|---|
| Organ distribution of [$^{18}$F]6a (% dose/g, avg of 3 mice ± SD) | | | | | |
| Organ | | | | | |
| Blood | 2.68 ± 0.37 | 2.05 ± 0.17 | 2.27 ± 0.11 | 1.75 ± 0.16 | 1.38 ± 0.20 |
| Heart | 4.49 ± 0.85 | 1.99 ± 0.19 | 2.14 ± 0.11 | 1.53 ± 0.15 | 1.22 ± 0.13 |
| Muscle | 0.66 ± 0.10 | 1.01 ± 0.02 | 1.52 ± 0.07 | 1.05 ± 0.03 | 0.73 ± 0.13 |
| Lung | 5.83 ± 1.25 | 2.96 ± 0.30 | 2.83 ± 0.25 | 1.74 ± 0.04 | 1.29 ± 0.19 |
| Kidney | 10.7 ± 3.06 | 5.51 ± 1.55 | 4.18 ± 0.33 | 2.27 ± 0.39 | 1.40 ± 0.30 |
| Spleen | 8.11 ± 0.90 | 2.77 ± 0.33 | 2.62 ± 0.20 | 1.56 ± 0.07 | 1.06 ± 0.10 |
| Liver | 18.2 ± 4.14 | 10.5 ± 1.48 | 8.85 ± 1.34 | 3.88 ± 0.40 | 3.36 ± 0.32 |
| Skin | 0.91 ± 0.10 | 1.19 ± 0.03 | 1.72 ± 0.11 | 1.23 ± 0.06 | 0.85 ± 0.10 |
| Brain | 4.66 ± 0.78 | 2.10 ± 0.25 | 2.09 ± 0.09 | 1.51 ± 0.20 | 1.13 ± 0.10 |
| Bone | 2.07 ± 0.05 | 2.40 ± 0.23 | 3.88 ± 0.47 | 5.84 ± 1.42 | 8.89 ± 0.75 |

TABLE 2-continued

Biodistribution of [$^{18}$F]6a and [$^{18}$F]6b in normal mice (iv injection)

|  | 2 min | 15 min | 30 min | 1 hr | 2 hr |
|---|---|---|---|---|---|
| Regional brain distribution | | | | | |
| *Region* | | | | | |
| Cerebellum (CB) | 4.42 ± 0.74 | 1.97 ± 0.22 | 1.97 ± 0.14 | 1.85 ± 0.20 | 1.09 ± 0.03 |
| Striatum | 5.46 ± 0.80 | 3.76 ± 0.51 | 3.37 ± 0.06 | 3.17 ± 0.79 | 1.39 ± 0.03 |
| Hippocampus | 4.84 ± 0.72 | 2.33 ± 0.30 | 2.02 ± 0.10 | 1.95 ± 0.49 | 1.22 ± 0.18 |
| Cortex | 4.70 ± 0.66 | 1.82 ± 0.19 | 1.96 ± 0.14 | 2.07 ± 0.42 | 0.88 ± 0.21 |
| Ratio (vs CB) | | | | | |
| Striatum | 1.23 | 1.91 | 1.71 | 1.71 | 1.28 |
| Hippocampus | 1.09 | 1.18 | 1.03 | 1.05 | 1.12 |
| Cortex | 1.06 | 0.92 | 1.00 | 1.12 | 0.81 |
| Organ distribution of [$^{18}$F]6b (% dose/g, avg of 3 mice ± SD) | | | | | |
| *Organ* | | | | | |
| Blood | 2.60 ± 0.31 | 1.75 ± 0.07 | 1.92 ± 0.22 | 1.04 ± 0.07 | 0.56 ± 0.07 |
| Heart | 6.79 ± 1.49 | 2.43 ± 0.16 | 2.67 ± 0.26 | 1.74 ± 0.14 | 1.02 ± 0.09 |
| Muscle | 1.17 ± 0.16 | 1.16 ± 0.35 | 1.53 ± 0.16 | 1.05 ± 0.41 | 0.56 ± 0.11 |
| Lung | 7.97 ± 1.46 | 3.58 ± 0.33 | 3.46 ± 0.36 | 2.15 ± 0.12 | 1.40 ± 0.09 |
| Kidney | 16.1 ± 3.13 | 5.90 ± 0.25 | 6.80 ± 0.65 | 3.63 ± 0.30 | 2.40 ± 0.51 |
| Spleen | 9.19 ± 0.26 | 3.38 ± 0.49 | 3.40 ± 0.43 | 2.05 ± 0.05 | 1.15 ± 0.41 |
| Liver | 24.1 ± 4.93 | 15.8 ± 1.65 | 17.3 ± 2.00 | 10.4 ± 0.95 | 8.53 ± 1.73 |
| Skin | 1.13 ± 0.25 | 1.15 ± 0.16 | 2.22 ± 0.20 | 1.38 ± 0.03 | 1.24 ± 0.53 |
| Brain | 7.08 ± 2.17 | 2.01 ± 0.10 | 1.76 ± 0.27 | 0.91 ± 0.25 | 0.53 ± 0.05 |
| Bone | 2.70 ± 0.44 | 3.65 ± 0.49 | 9.62 ± 3.42 | 16.6 ± 1.60 | 17.8 ± 1.83 |
| Regional brain distribution | | | | | |
| *Region* | | | | | |
| Cerebellum (CB) | 6.26 ± 2.89 | 1.63 ± 0.05 | 1.30 ± 0.19 | 0.77 ± 0.06 | 0.45 ± 0.01 |
| Striatum | 8.49 ± 1.12 | 4.12 ± 0.52 | 3.84 ± 1.05 | 2.08 ± 0.27 | 0.87 ± 0.24 |
| Hippocampus | 7.07 ± 1.66 | 2.14 ± 0.16 | 2.55 ± 1.20 | 1.04 ± 0.16 | 0.50 ± 0.06 |
| Cortex | 8.25 ± 2.51 | 1.62 ± 0.05 | 1.45 ± 0.38 | 0.85 ± 0.12 | 0.41 ± 0.06 |
| Ratio (vs CB) | | | | | |
| Striatum | 1.36 | 2.53 | 2.95 | 2.71 | 1.94 |
| Hippocampus | 1.13 | 1.31 | 1.97 | 1.35 | 1.12 |
| Cortex | 1.32 | 1.00 | 1.11 | 1.10 | 0.91 |

TABLE 3

Biodistribution in normal mice at 30 min. after an iv injection of [$^{18}$F]6b in saline with 3 mg/kg of (+)DTBZ or 1.2 mg/kg of raclopride

|  | Control | (+)-DTBZ | raclopride |
|---|---|---|---|
| Organ distribution (% dose/g, avg of 3 mice ± SD) | | | |
| *Organ* | | | |
| Blood | 1.41 ± 0.20 | 1.67 ± 0.04 | 1.60 ± 0.08 |
| Heart | 2.05 ± 0.13 | 2.36 ± 0.07 | 2.29 ± 0.06 |
| Muscle | 1.06 ± 0.06 | 1.28 ± 0.07 | 1.15 ± 0.03 |
| Lung | 2.78 ± 0.20 | 3.27 ± 0.17 | 3.34 ± 0.24 |
| Kidney | 5.90 ± 0.42 | 4.94 ± 3.38 | 6.01 ± 0.50 |
| Spleen | 2.90 ± 0.14 | 2.67 ± 0.17 | 3.25 ± 0.20 |
| Liver | 13.9 ± 1.15 | 14.0 ± 0.56 | 14.6 ± 0.44 |
| Skin | 1.48 ± 0.09 | 1.67 ± 0.02 | 1.58 ± 0.09 |
| Brain | 1.40 ± 0.12 | 0.86 ± 0.04 | 1.64 ± 0.16 |
| Bone | 6.06 ± 1.11 | 6.54 ± 0.84 | 6.03 ± 1.07 |
| Regional brain distribution | | | |
| *Region* | | | |
| Cerebellum (CB) | 1.05 ± 0.09 | 0.89 ± 0.16 | 1.19 ± 0.11 |
| Striatum | 3.57 ± 0.30 | 0.87 ± 0.18 | 4.67 ± 1.29 |
| Hippocampus | 1.43 ± 0.12 | 0.83 ± 0.27 | 1.89 ± 0.85 |
| Cortex | 1.21 ± 0.15 | 0.91 ± 0.13 | 1.41 ± 0.15 |
| Hypothalamus | 2.67 ± 0.30 | 0.92 ± 0.23 | 2.52 ± 0.77 |
| Ratio (vs CB) | | | |
| Striatum | 3.40 | 0.98 | 3.93 |
| Hippocampus | 1.36 | 0.94 | 1.59 |
| Cortex | 1.15 | 1.03 | 1.18 |
| Hypothalamus | 2.54 | 1.04 | 2.12 |

EXAMPLE 7

Organ Distribution of [$^{18}$F]FP-(±)-6b in Normal Mice

After anesthetizing ICR mice (22-25 g male) with isoflurane, 0.15 mL of a 0.1% bovine serum albumin solution containing [$^{18}$F]FP-(+)-6b (10-20 µCi) was injected directly into the tail vein. The mice (n=3 for each time point) were sacrificed by cervical dislocation (under isoflurane anesthesia) at indicated time-points post-injection. The organs of interest were removed and weighed, and the radioactivity was counted with an automatic gamma counter. The percentage dose per organ was calculated by a comparison of the tissue counts to suitably diluted aliquots of the injected material. The total activity of the blood was calculated under the assumption that it was 7% of the total body weight. The % does/g of samples was calculated by comparing the sample counts with the count of the diluted initial dose. Different regions corresponding to striatum (ST), hippocampus (HP), cerebellum (CB), and cortex (CX) were dissected from the brain and counted to obtain the regional distribution of the tracer.

Four lesioned mice were injected with a mixture of 20 µCi each of [$^{18}$F]FP-(+)-DTBZ and [$^{125}$I] PT (N-(3'-iodopropen-2'-yl)-2-beta-carbomethoxy-3-beta-(4-chlorophenyl)tropane, a dopamine transporter ligand). Thirty minutes after injection, the mice were sacrificed and the brains removed. Different regions corresponding to striatum (ST), hippocampus (HP), cerebellum (CB), and cortex (CX) were dissected. In particular, the lesioned region was separated from non-lesioned area of the striatal tissues. Samples were counted in a gamma counter with two different window settings for F-18 and I-125, respectively, to obtain the regional distribution of each tracer.

TABLE 4

Biodistribution of [$^{18}$F]FP-(±)-6b in normal mice
(% dose/g, avg of 3 mice ± SD)

| | 2 min | 30 min | 60 min | 2 hr | 4 hr |
|---|---|---|---|---|---|
| Organ distribution | | | | | |
| Organ | | | | | |
| Blood | 2.12 ± 0.17 | 1.73 ± 0.15 | 0.97 ± 0.04 | 0.57 ± 0.09 | 0.06 ± 0.02 |
| Heart | 5.47 ± 1.19 | 2.43 ± 0.22 | 1.67 ± 0.02 | 0.91 ± 0.14 | 0.12 ± 0.01 |
| Muscle | 0.78 ± 0.11 | 1.10 ± 0.12 | 0.73 ± 0.04 | 0.53 ± 0.05 | 0.06 ± 0.01 |
| Lung | 9.04 ± 4.71 | 3.17 ± 0.33 | 2.00 ± 0.05 | 1.26 ± 0.13 | 0.19 ± 0.01 |
| Kidney | 10.7 ± 2.02 | 5.81 ± 1.15 | 3.48 ± 0.34 | 2.28 ± 0.34 | 0.31 ± 0.02 |
| Spleen | 7.38 ± 1.62 | 3.69 ± 0.25 | 2.11 ± 0.05 | 1.40 ± 0.35 | 0.17 ± 0.02 |
| Liver | 24.6 ± 1.37 | 22.2 ± 1.98 | 14.5 ± 0.91 | 9.81 ± 0.94 | 1.58 ± 0.08 |
| Skin | 1.05 ± 0.12 | 1.42 ± 0.03 | 1.06 ± 0.04 | 0.67 ± 0.06 | 0.09 ± 0.01 |
| Brain | 4.82 ± 0.86 | 2.05 ± 0.37 | 1.10 ± 0.32 | 0.68 ± 0.11 | 0.16 ± 0.03 |
| Bone | 1.95 ± 0.30 | 4.88 ± 1.43 | 9.22 ± 0.48 | 12.7 ± 1.84 | 3.49 ± 0.35 |
| Regional brain distribution (% dose/g) | | | | | |
| Region | | | | | |
| Cerebellum (CB) | 4.67 ± 0.74 | 1.41 ± 0.23 | 0.89 ± 0.01 | 0.54 ± 0.09 | 0.41 ± 0.02 |
| Striatum | 7.28 ± 0.80 | 6.34 ± 1.01 | 4.24 ± 0.78 | 1.76 ± 0.33 | 0.46 ± 0.13 |
| Hippocampus | 4.54 ± 0.72 | 2.23 ± 0.59 | 1.18 ± 0.12 | 0.58 ± 0.15 | 0.41 ± 0.01 |
| Cortex | 4.54 ± 0.66 | 1.88 ± 0.63 | 0.89 ± 0.04 | 0.51 ± 0.02 | 0.36 ± 0.02 |
| Remainder | 4.71 ± 0.74 | 2.04 ± 0.28 | 1.30 ± 0.08 | 0.62 ± 0.10 | 0.42 ± 0.05 |
| Hypothalamus | 6.41 ± 1.11 | 4.95 ± 0.84 | 2.42 ± 0.52 | 1.02 ± 0.11 | 0.47 ± 0.01 |
| Ratio (vs CB) | | | | | |
| Striatum | 1.56 | 4.51 | 4.74 | 3.28 | 1.11 |
| Hippocampus | 0.97 | 1.59 | 1.32 | 1.09 | 0.99 |
| Cortex | 0.97 | 1.34 | 1.00 | 0.96 | 0.87 |
| Remainder | 1.01 | 1.45 | 1.45 | 1.15 | 1.02 |
| Hypothalamus | 1.37 | 3.52 | 2.71 | 1.90 | 1.15 |

TABLE 5

Biodistribution of [$^{18}$F]FP-(±)-6b in normal rats (% dose/g)

| | 2 min | 30 min | 60 min | 120 min |
|---|---|---|---|---|
| Blood | 0.26 ± 0.03 | 0.23 ± 0.06 | 0.18 ± 0.02 | 0.12 ± 0.03 |
| Heart | 0.71 ± 0.07 | 0.41 ± 0.03 | 0.30 ± 0.10 | 0.22 ± 0.01 |
| Muscle | 0.14 ± 0.03 | 0.17 ± 0.02 | 0.13 ± 0.01 | 0.10 ± 0.01 |
| Lung | 0.94 ± 0.04 | 0.69 ± 0.03 | 0.54 ± 0.14 | 0.35 ± 0.03 |
| Kidney | 2.10 ± 0.17 | 1.06 ± 0.06 | 0.84 ± 0.09 | 0.55 ± 0.06 |
| Pancreas | 2.51 ± 0.22 | 5.50 ± 0.97 | 4.98 ± 0.24 | 2.76 ± 0.61 |
| Spleen | 1.46 ± 0.15 | 1.03 ± 0.18 | 0.83 ± 0.18 | 0.48 ± 0.04 |
| Liver | 3.53 ± 0.56 | 2.82 ± 0.24 | 2.47 ± 0.30 | 1.47 ± 0.13 |
| Skin | 0.23 ± 0.05 | 0.28 ± 0.01 | 0.23 ± 0.04 | 0.16 ± 0.02 |
| Brain | 0.71 ± 0.05 | 0.62 ± 0.08 | 0.42 ± 0.04 | 0.35 ± 0.02 |
| Cerebellum | 0.63 ± 0.03 | 0.40 ± 0.04 | 0.28 ± 0.04 | 0.20 ± 0.01 |
| Striatum | 1.52 ± 0.20 | 2.25 ± 0.48 | 1.85 ± 0.26 | 1.42 ± 0.54 |
| Hippocampus | 0.68 ± 0.07 | 0.61 ± 0.12 | 0.36 ± 0.08 | 0.23 ± 0.03 |
| Cortex | 0.65 ± 0.02 | 0.44 ± 0.06 | 0.27 ± 0.07 | 0.20 ± 0.06 |

EXAMPLE 8

Organ Distribution of [$^{18}$F](+)-6b in Normal Rats

The ability of (+)-6b to target the pancreas was shown in normal rats. Using the methods described above under Example 6, the biodistribution of (+)-6b after IV injection in twelve normal rats was measured. The results are shown in Table 5. For the organs studied, the pancreas had the highest % dose/gram within 30 minutes after injection. Also shown are data indicating distribution in the striatum, which is another area rich in VMAT-2 receptors.

EXAMPLE 9

Blocking Studies for Specific Pancreatic Targeting

Competition studies were performed to demonstrate the specificity of the imaging seen in the pancreas. Rats were pretreated with non-radiolabeled DBTZ (3.8 mg/kg) five minutes prior to injection with (+)-6b. The biodistribution experiment was carried out as described above in Example 6. Levels of (+)-6b were significantly lower in target organs as a result of being blocked by the presence of non-radiolabeled DBTZ.

TABLE 6

Blocking of [$^{18}$F]-(+)-6b Pancreatic Signal by DTBZ
(% dose/g at 30 mins, average ± SD)

|  | 30 min Control | 30 min Blocking |
|---|---|---|
| Blood | 0.20 ± 0.01 | 0.32 ± 0.04 |
| Pancreas | 4.39 ± 0.64 | 3.10 ± 0.30 (30% Blocking) |
| Regional Brain Distribution (% dose/gram ± SD) | | |
| Cerebellum | 0.36 ± 0.00 | 0.25 ± 0.03 |
| Striatum | 1.94 ± 0.03 | 0.27 ± 0.02 (>90% Blocking) |
| Hippocampus | 0.54 ± 0.03 | 0.25 ± 0.03 |
| Cortex | 0.36 ± 0.00 | 0.26 ± 0.05 |
| Hypothalamus | 1.20 ± 0.07 | 0.25 ± 0.04 |

EXAMPLE 10

Dual Isotope Experiment in Lesioned Mice

The ratios of target (ST) vs nontarget (CB) were compared between control and blocked groups.

To measure the degree of lesion, a dual-isotope experiment comparing the striatal uptakes in lesioned vs. unlesioned sites using [$^{18}$F]FP-DTBZ was performed. A marker [$^{125}$I]IPT (selective for dopamine transporters) was injected simultaneously. The mice showed a range of neuronal damage, from slight lesion to severe lesion, as evidenced by reduced binding of both radiotracers in the lesioned side. Lower uptakes in the lesioned sites as measured by [$^{18}$F]FP-DTBZ (VMAT2 sites) correlated very well with the data obtained with [$^{125}$I]IPT (DAT sites)(r 0.95). The results are shown below in Table 7.

TABLE 7

Dual Isotope Experiment with [$^{18}$F]FP-6b and [$^{125}$I]IPT in Lesioned Mice
Regional brain distribution (% dose/g) and
[ratio vs. CB] measured at 30 min post-injection

|  | Mouse 1 | Mouse 2 | Mouse 3 | Mouse 4 |
|---|---|---|---|---|
| [$^{18}$F]FP-DTBZ | | | | |
| Cerebellum (CB) | 1.58 [1.00] | 1.62 [1.00] | 1.26 [1.00] | 1.76 [1.00] |
| Striatum L | 3.36 [2.13] | 4.12 [2.54] | 4.17 [3.30] | 8.03 [4.57] |
| Stratum N | 8.46 [5.37] | 6.29 [3.87] | 7.28 [5.76] | 8.90 [5.07] |
| Hippocampus | 2.95 [1.87] | 3.00 [1.85] | 2.24 [1.78] | 3.00 [1.71] |
| Cortex | 1.53 [0.97] | 1.51 [0.93] | 1.31 [1.04] | 1.94 [1.10] |
| Remainder | 2.30 [1.46] | 2.24 [1.38] | 2.06 [1.63] | 2.45 [1.39] |
| Hypothalamus | 5.19 [3.29] | 5.04 [3.10] | 4.01 [3.18] | 5.68 [3.23] |
| *% StrL/StrN | 39.7 | 65.6 | 57.3 | 90.1 |
| [$^{125}$I]IPT | | | | |
| Cerebellum (CB) | 0.96 [1.00] | 0.77 [1.00] | 0.81 [1.00] | 0.76 [1.00] |
| Striatum L | 3.00 [3.14] | 3.53 [4.55] | 4.75 [5.90] | 6.89 [9.07] |
| Stratum N | 9.21 [9.63] | 6.33 [8.17] | 9.09 [11.3] | 7.77 [10.2] |
| Hippocampus | 0.87 [0.91] | 0.70 [0.90] | 0.81 [1.00] | 0.62 [0.81] |
| Cortex | 0.69 [0.72] | 0.62 [0.80] | 0.66 [0.81] | 0.87 [1.15] |
| Remainder | 1.34 [1.40] | 1.16 [1.49] | 1.57 [1.95] | 1.16 [1.53] |
| Hypothalamus | 1.28 [1.34] | 1.22 [1.58] | 1.42 [1.76] | 0.99 [1.31] |
| *% StrL/StrN | 32.6 | 55.7 | 52.3 | 88.7 |

EXAMPLE 11

Partition Coefficient

Partition coefficients were measured by mixing the [$^{18}$F] tracer with 3 g each of 1-octanol and buffer (0.1 M phosphate, pH 7.4) in a test tube. The test tube was vortexed for 3 min at room temperature, followed by centrifugation for 5 min. Two weighed samples (0.5 g each) from the 1-octanol and buffer layers were counted in a well counter. The partition coefficient was determined by calculating the ratio of cpm/g of 1-octanol to that of buffer. Samples from the 1-octanol layer were re-partitioned until consistent partitions of coefficient values were obtained. Values are the mean±SEM of three independent experiments, each in duplicates.

EXAMPLE 12

Homogenate Binding of (+)-6b

The basal forebrain tissues containing the striatal region were dissected and remover from frozen rat brains. The brain tissue homogenates were prepared in 50 mM Hepes, pH 7.5 and 0.32 M sucrose. The specific binding of [$^3$H]±TBZ was determined following a reported procedure (Scherman D, et al., [$^3$H]Dihydrotetrabenazine, a new in vitro monoaminergic probe for human brain, *J. Neurochem.* 1988; 50:1131-36). The total volume of reaction for the assay was 0.2 mL. In competition experiments, compounds at concentrations up to $10^{-5}$ M were examined for their abilities to compete for the binding of [$^3$H]±TBZ (1.0-1.5 nM). Incubations were carried out routinely at room temperature for 90 min. The samples were filtered through glass fiber filters No. 25. Filters containing bound 3H ligand were dissolved in 7 ml Ecolite(+) overnight, and the radioactivity was counted the next day in a scintillation counter with 65% counting efficiency. Nonspecific binding was determined in the presence of 10 μM (±)-TBZ. The results of inhibition experiments were subjected to nonlinear regression analysis using equilibrium binding data analysis by which $K_i$ values were calculated.

TABLE 8

Inhibition constants ($K_i$, mean ± SEM) of FP-(±)-DTBZ, FP-(+)-DTBZ and FP-(−)-DTBZ on [$^3$H](±)-TBZ binding to VMAT2 in rat striatal homogenates.

| Compound | $K_i$ (nM) |
|---|---|
| FP-(±)-DTBZ | 0.19 ± 0.04 |
| FP-(+)-DTBZ | 0.10 ± 0.01 |
| FP-(−)-DTBZ | >3000 |
| (±)-TBZ | 1.3 ± 0.1 |

$K_d$ value of 8.2 nM for [$^3$H](±)-TBZ was used for the calculation based on the $K_i$ value reported (Kilbourn, M, Sherman P, In vivo binding of (+)-[alpha]-[$^3$H]dihydrotetrabenazine to the vesicular monoamine transporter of rat brain: bolus vs. equilibrium studies, *Eur. J. Pharmacol.*, 1997; 331: 161-68). The results are means ± SEM of three independent measures done in duplicate.

EXAMPLE 13

Ex Vivo Autoradiographic Studies

Figure 3:
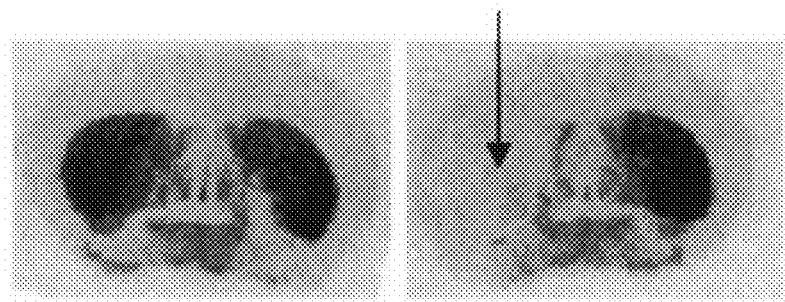
FIG. 3 depicts an ex vivo autoradiography (30 minutes post-injection) of [$^{18}$F]FP-(+)-DTBZ differentiating the lesioned (L, indicated by an arrow) from the unlesioned side (N) in the brains of 6-OH-DA unilaterally lesioned mice. 300 µCi [$^{18}$F]FP-(+)-DTBZ was injected and animals were sacrificed at 30 minutes post-injection.
Figure 4:
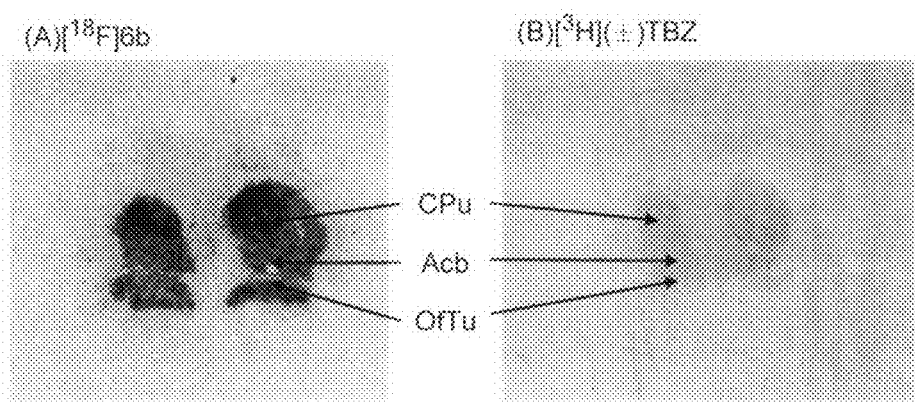
FIG. 4 depicts an autoradiographic scan of in vitro localization in the mouse brain of a representative compound, 6b of the present invention. Sections were incubated at RT for 90 min with 1.2 nM [$^{18}$F]6b or 4.6 nM [$^{3}$H](±)DTBZ. CPu: caudate putamen; Acb: nucleus accumbens; Of. Tu.: olfactory tubercle
Figure 5:
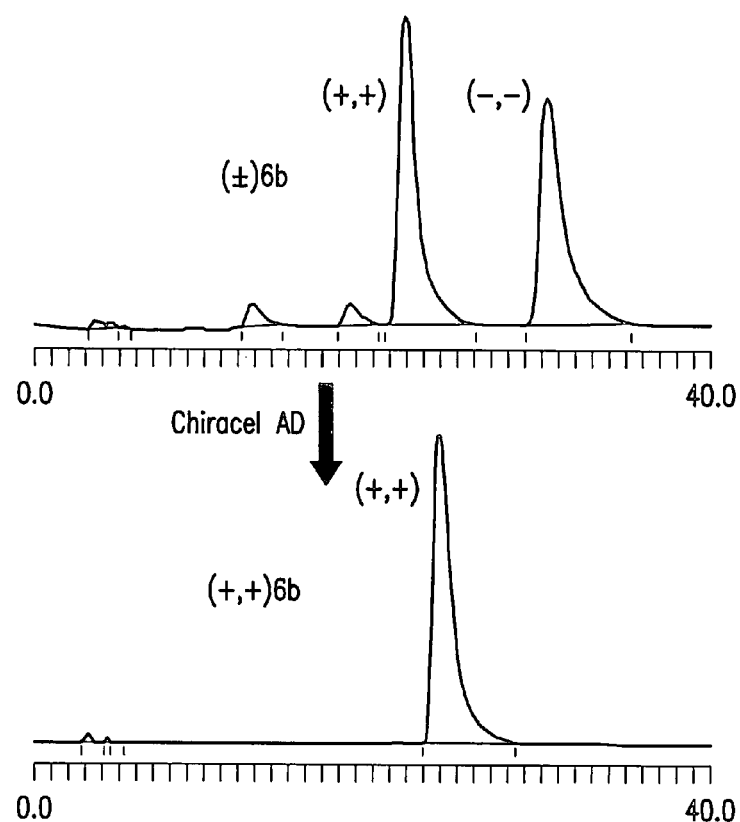
FIG. 5 depicts chiral HPLC separation of (+)-6b from a racemic mixture.
Figure 6:
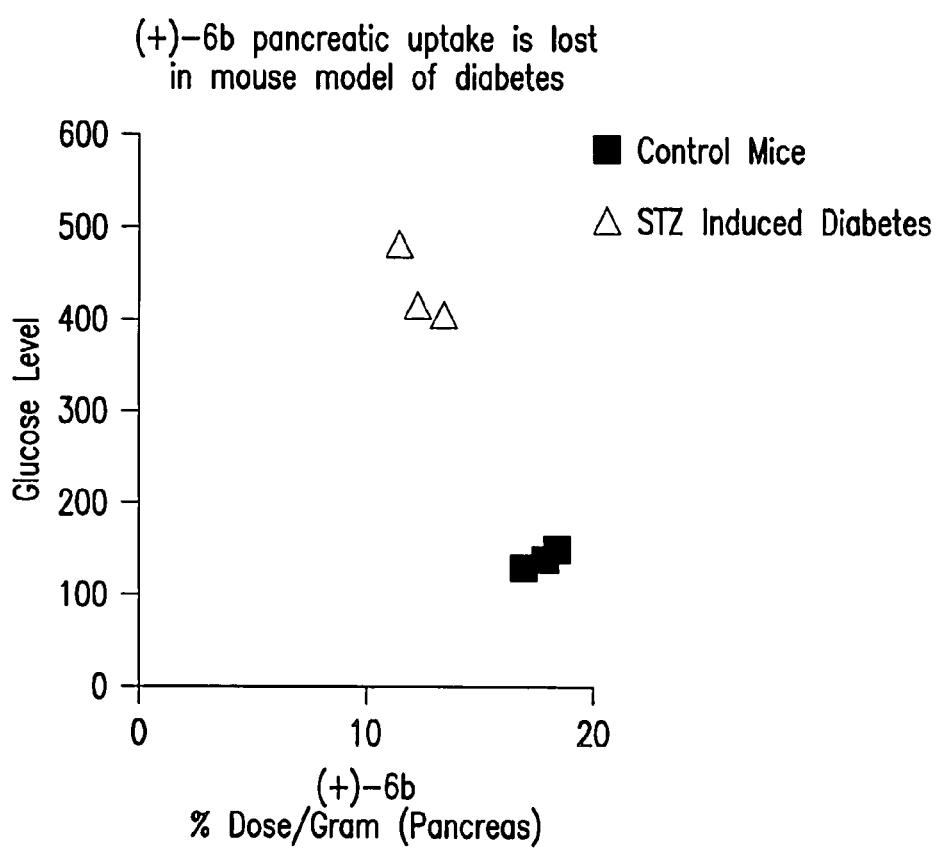
FIG. 6 depicts data that show the uptake of (+)-6b is reduced in diabetic mice, correlating to a lower BCM in diabetic states.
Figure 7:
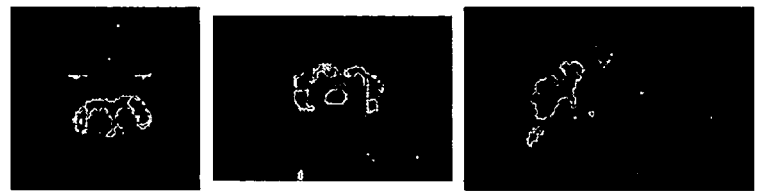
FIG. 7 depicts baboon microPET imaging after iv injection of [$^{18}$F]FP-(+)-6b (7 mCi injection); data collected between 70-90 min showing striatal uptakes and no indication of skull (bone) uptake.
Figure 8:
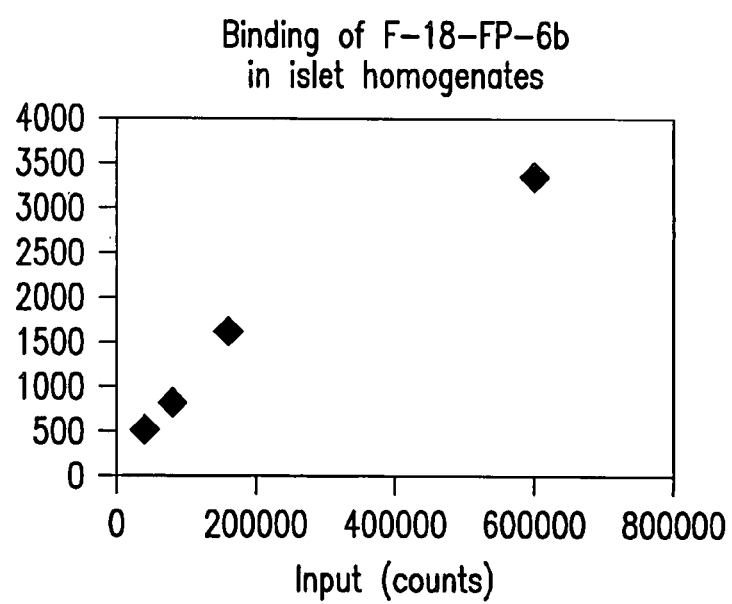
FIG. 8 depicts in vitro binding of [$^{18}$F]-(+)-6b to islet cell homogenates indicating that binding is specific and saturable.
Figure 9:
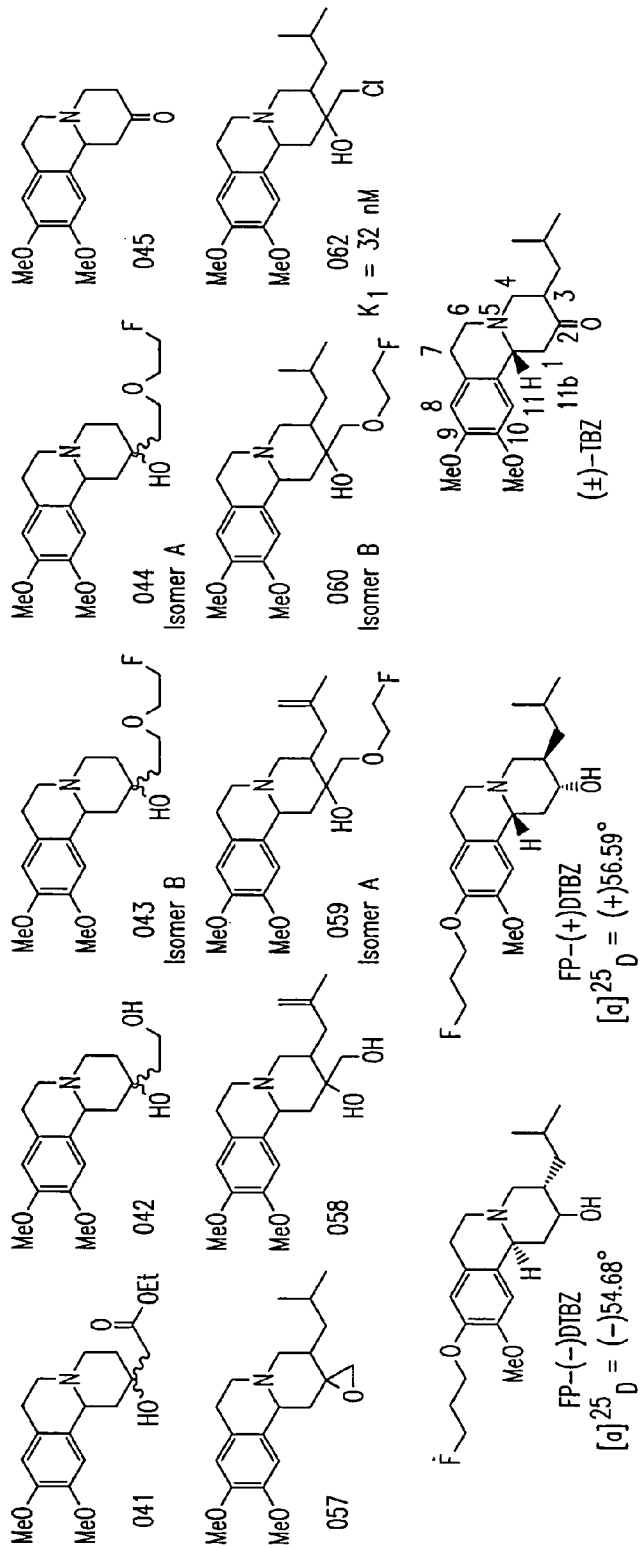
FIG. 9 depicts the structures and binding data of certain compounds of the invention.
Figure 10:
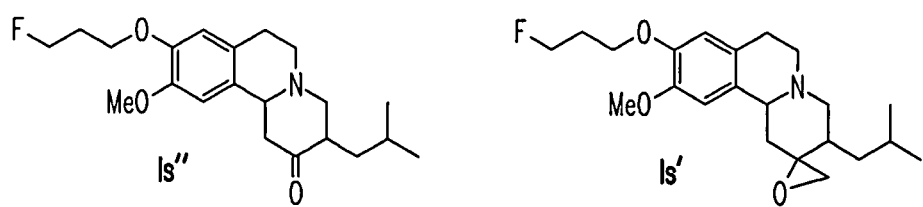
FIG. 10 depicts the structures and binding data ($K_i$ on $^3$H-TBZ binding to VMAT2 (rat striatal homogenates)) of certain fluoropropyl keto and epoxide derivatives of the invention.

Both normal and ICR mice and lesioned mice were injected with 200-400 μCi [$^{18}$F]FP-(±)-DTBZ and sacrificed 30 minutes post-injection. The brains were then removed immediately and frozen with powdered dry ice. Coroanl sections of 20 μm thickness were cut on a cryostat microtome, thaw-mounted onto Fisher Superfrost Plus slides and dried at room temperature. The dried tissue sections were then exposed to Kodak Biomax MR film for $^{18}$F tracer (overnight) in an autoradiographic cassette together with 20 μm thick $^{125}$I, standards. These studies are depicted in FIGS. 2 and 3.

EXAMPLE 14

Metabolic Stability in Mouse Brain

Two mice were injected with 200 μCi [$^{18}$F]FP-(+)-DTBZ and sacrificed at 30 minutes post-injection. The brains were removed and the striatal regions were dissected out. The striatal homogenates (prepared in PBS, 10% w/v) were extracted with 0.5 mL of ethyl acetate in the presence of a small amount of carrier (10 μg of [$^{18}$F]FP-(±)-DTBZ). Extraction was repeated three times and the ethyl acetate layers and the buffer layers were counted separately to determine the percent extracted. After condensing the ethyl acetate layers, the samples were analyzed on TLC (Silica 254F plate with the developing solvent of chloroform/ethanol/con.ammonium=8/2/drop) for metabolite identification. A control sample ([$^{18}$F]FP-(±)-DTBZ mixed with normal mouse striatal homogenates in situ) was carried out in parallel for comparison. The data indicated that less than 5% degradation.

EXAMPLE 15

Non-Labeled (+)-6b Binding Affinity for VMAT-2

Using rat striatal tissue homogenates, non-labeled (+)-6b at concentrations up to $10^{-5}$ M were competed against [$^{3}$H](±)-TBZ (1.0-1.5 nM), a known ligand for VMAT-2. Incubations were carried out at room temperature for 90 min. The samples were then filtered through glass fiber filters (No. 25) and the filters containing bound $^{3}$H ligand were dissolved in 7 ml Ecolite (+) overnight. Radioactivity was counted in a scintillation counter (Beckman) with 65% counting efficiency. Nonspecific binding was determined in the presence of 10 μM (±)-TBZ. The results of inhibition experiments were subjected to nonlinear regression analysis using equilibrium binding data analysis by which $K_i$ values were calculated. Based on the published $K_d$ value of 8.1 nM (Goswami, 2006) for [$^{3}$H](±)-TBZ, the binding affinity of (+)-6b was found to be 0.10 nM.

EXAMPLE 16

Radiation Dosimetry Estimates

From the organ biodistribution data in Table 4 of Example 7, human radiation dosimetry estimates were calculates. In the mass based extrapolation, the concentration in the animal organs is converted to a concentration in human organs by multiplying the animal concentration by a ratio of the total body weight of the animals and humans (Kirschner, et al., 1975). Then the percent in the human organs is derived using organ masses taken from a standard model of the human body for adult males (Cristy and Eckerman, 1987). Data were fit using the SAAM II software (Foster and Barrett, 1999). Time integrals of activity were calculated and converted to residence times (Loevinger, et al., 1988); organ residence times were entered into the OLIND/EXM software (STabin, et al., 2005) using the adult male model. No excretion of activity was assumed; any activity not accounted for was considered to be uniformly distributed throughout the remainder of the body or removed only by physical decay. Based on this methodology, the human radiation dose estimates for [$^{18}$F]-(+)-6b indicate that most organs receive around 0.04-0.06 rem/mCi, with liver and bone surface receiving a slightly higher dose, around 0.11 rem/mCi. The estimated effective dose (0.047 rem/mCi) also compares favorably to radiation doses received with other approved radiopharmaceuticals. The radiation dose estimates are shown in Table 9 below.

TABLE 9

Human Radiation Dose Estimates for [$^{18}$F]-(+)-6b

| Target Organ | Estimated Dose mSv/MBq | rem/mCi |
|---|---|---|
| Adrenals | 1.38E-02 | 5.09E-02 |
| Brain | 3.01E-03 | 1.11E-02 |
| Breasts | 9.14E-03 | 3.38E-02 |
| Gallbladder Wall | 1.57E-02 | 5.80E-02 |
| LLI Wall | 1.31E-02 | 4.84E-02 |
| Small Intestine | 1.36E-02 | 5.02E-02 |
| Stomach Wall | 1.27E-02 | 4.70E-02 |
| ULI Wall | 1.35E-02 | 4.99E-02 |
| Heart Wall | 9.78E-03 | 3.62E-02 |
| Kidneys | 1.24E-02 | 4.57E-02 |
| Liver | 2.72E-02 | 1.01E-01 |
| Lungs | 9.28E-03 | 3.43E-02 |
| Muscle | 1.10E-02 | 4.05E-02 |
| Ovaries | 1.35E-02 | 5.01E-02 |
| Pancreas | 1.41E-02 | 5.22E-02 |
| Red Marrow | 1.48E-02 | 5.48E-02 |
| Osteogenic Cells | 3.11E-02 | 1.15E-01 |
| Skin | 8.59E-03 | 3.18E-02 |
| Spleen | 9.73E-03 | 3.60E-02 |
| Testes | 1.07E-02 | 3.98E-02 |
| Thymus | 1.12E-02 | 4.16E-02 |
| Thyroid | 1.12E-02 | 4.14E-02 |
| Urinary Bladder Wall | 1.29E-02 | 4.76E-02 |
| Uterus | 1.36E-02 | 5.04E-02 |
| Total Body | 1.19E-02 | 4.42E-02 |
| Effective Dose Equivalent | 1.40E-02 | 5.17E-02 |
| Effective Dose (mSv/MBq) | 1.27E-02 | 4.69E-02 |

Having now fully described this invention, it will be understood to those of ordinary skill in the art that the same can be performed within a wide and equivalent range of conditions, formulations, and other parameters without affecting the scope of the invention or any embodiment thereof. All patents, patent applications, and publications cited herein are fully incorporated by reference herein in their entirety.

What is claimed is:

1. A compound of the formula

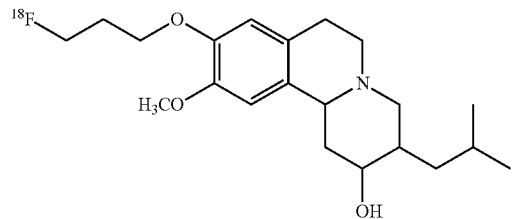 [SMILES: COc1cc2c(cc1OCCC[18F])CCN1CC(CC(C)C)C(O)CC21]

or a pharmaceutically acceptable salt thereof.

2. A compound of the formula or a pharmaceutically acceptable salt thereof.

3. A compound of the formula

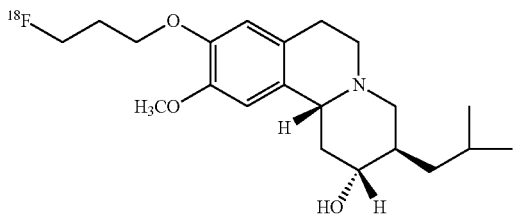 [SMILES: COc1cc2c(cc1OCCC[18F])CCN1C[C@@H](CC(C)C)[C@H](O)C[C@H]21]

or a pharmaceutically acceptable salt thereof.

4. The compound of claim 3, having no less than about 95% stereochemical purity.

5. A diagnostic composition comprising a labeled compound of formula:

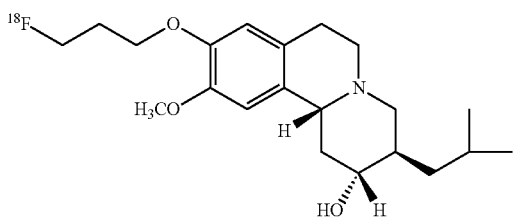 [SMILES: COc1cc2c(cc1OCCC[18F])CCN1C[C@@H](CC(C)C)[C@H](O)C[C@H]21]

or a pharmaceutically acceptable salt thereof, and a pharmaceutically acceptable carrier or diluent.

6. A compound of the formula

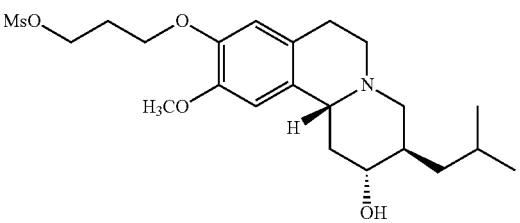

wherein Ms is methanesulfonyl.

7. A compound of the formula

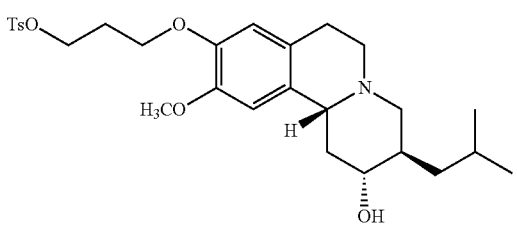

wherein Ts is p-toluenesulfonyl.

8. A process of making a compound of the formula:

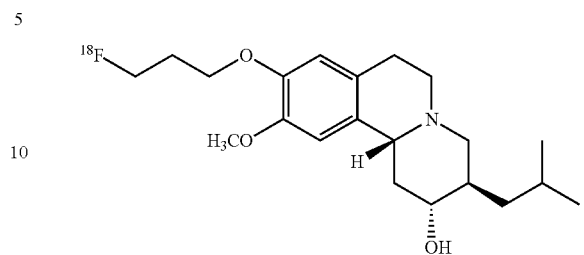

[$^{18}$F]-(+)-6b comprising reacting a compound of the formula

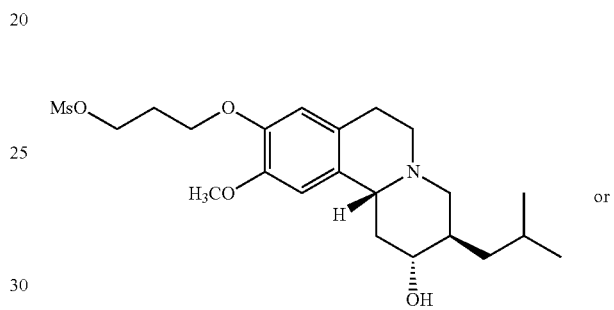

with $^{18}$F anion, wherein Ms is methanesulfonyl and Ts is p-toluenesulfonyl.

9. A method of imaging vesicular monoamine transporters, comprising:
  a. introducing into a mammal a detectable quantity of the diagnostic composition of claim 5;
  b. allowing sufficient time for said labeled compound to become associated with said transporters; and
  c. detecting the labeled compound.

* * * * *